US008398990B2

(12) United States Patent
Cassone et al.

(10) Patent No.: US 8,398,990 B2
(45) Date of Patent: *Mar. 19, 2013

(54) GLUCAN-BASED VACCINES

(75) Inventors: Antonio Cassone, Rome (IT); Luciano Polonelli, Parma (IT)

(73) Assignees: Antonio Cassone, Rome (IT); Luciano Polonelli, Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/854,248

(22) Filed: Aug. 11, 2010

(65) Prior Publication Data

US 2011/0059120 A1 Mar. 10, 2011

Related U.S. Application Data

(60) Continuation of application No. 11/701,250, filed on Feb. 1, 2007, now Pat. No. 7,824,688, which is a division of application No. 10/514,483, filed as application No. PCT/IB03/02460 on May 15, 2003, now abandoned.

(30) Foreign Application Priority Data

May 15, 2002 (GB) .................................. 0211118.5

(51) Int. Cl.
A61K 39/00 (2006.01)
A61K 39/07 (2006.01)
A61K 39/385 (2006.01)
(52) U.S. Cl. .............. 424/193.1; 424/197.11; 424/274.1
(58) Field of Classification Search ........................ None
See application file for complete search history.

(56) References Cited

U.S. PATENT DOCUMENTS

| | | | |
|---|---|---|---|
| 4,795,745 | A | 1/1989 | Larm et al. |
| 5,306,492 | A | 4/1994 | Porro |
| 5,322,841 | A | 6/1994 | Jamas et al. |
| 6,309,642 | B1 | 10/2001 | Cutler et al. |

FOREIGN PATENT DOCUMENTS

| | | |
|---|---|---|
| JP | 61-118320 | 6/1986 |
| JP | 09-309842 | 12/1997 |
| WO | WO 95/30022 A1 | 11/1995 |
| WO | WO 96/28476 A1 | 9/1996 |
| WO | WO 99/55715 A2 | 11/1999 |

OTHER PUBLICATIONS

Askelof et al., "Protective immunogenicity of two synthetic peptides selected from the amino acid sequence of *Bordetella pertussis* toxin subunit S1," *PNAS USA* 87:1347-1351 (1990).
Crane et al., "Comparison of the diphtheria mutant toxin, CRM197, with a *Haemophilus influenzae* type-*b* polysaccharide-CRM197 conjugate by optical spectroscopy," *Eur J Biochem* 246:320-327 (1997).
Franz et al., "Novel Pharmaceutical Applications of Polysaccharides," *Macromol Symp* 99:187-200 (1995).
Galichet et al., "FTIR spectroscopic analysis of *Saccharomyces cerevisiae* cell walls: study of an anomalous strain exhibiting a pink-colored phenotype," *FEMS Micobiol Lett* 197:179-186 (2001).
Ho et al., "Solution stability studies of the subunit components of meningococcal C oligosaccharide-$CRM_{197}$ conjugate vaccines," *Biotechnol Appl Biochem* 33:91-98 (2001).
Kernodle et al., "Prophylactic Anti-Infective Activity of Poly-[1-6]-β-D-Glucopyranosyl-[1-3]-β-D-Glucopyranose Glucan in a Guinea Pig Model of Staphylococcal Wound Infection," *Antimicrobial Agents and Chemotherapy* 42(3):545-549 (1998).
Ohno et al., "Structure and biological activities of hypochlorite oxidized zymosan," *Carbohydrate Polymers* 44:339-349 (2001).
Onderdonk et al., "Anti-Infective Effect of Poly-β1-6-Glucotriosyl-β1-3-Glucopyranose Glucan In Vivo," *Infect & Immun* 60(4):1642-1647 (1992).
Adachi, et al., "Preparation and Antigen Specificity of an Anti-(1->3)-Beta-D-Glucan Antibody," *Biological and Pharmaceutical Bulletin* 17(11):1508-1512 (1994).
Bromuro, et al., "Interplay Between Protective and Inhibitory Antibodies Dictates the Outcome of Experimentally Disseminated Candidiasis in Recipients of a *Candida abicans* Vaccine," *Infection and Immunity* 70(10):5462-5470 (2002).
Casadevall, et al., "Antibody Immunity and Invasive Fungal Infections," *Infection and Immunity* 63(11):4211-4218 (1995).
Deepe, "Prospects for the Development of Fungal Vaccines," *Clinical Microbiology Reviews* 10(4):585-596 (1997).
Derwent Abstract for "Method Produce Cell Wall Skeleton Powder Red Norcia," *Derwent Publications Ltd.*, London, GB, One Page (1994) XP002264615.
Kieber-Emmons, "Peptide Mimotopes of Carbohydrate Antigens," *Immunologic Research* 17(1-2):95-108 (1998).
Kieber-Emmons, et al., "Cutting Edge:DNA Immunization with Minigenes of Carbohydrate Mimotopes Induce Functional Anti-Carbohydrate Antibody Response," *Journal of Immunology* 165(2):623-627 (2000).
Kondori, et al., "Candida Albicans Cell Wall Antigens for Serological Diagnosis of Candidemia," *Medical Mycology* 41(1):21-30 (2003).
Masuzawa, et al., "Solubilized Candida Cell Wall Beta-Glucan, CSBG, is an Epitope of Natural Human Antibody," *Drug Development Research* 58(2):179-189 (2003).

(Continued)

*Primary Examiner* — Brian J Gangle
(74) *Attorney, Agent, or Firm* — Roberta L. Robins; Robins Law Group

(57) ABSTRACT

Anti-glucan antibodies have been found to be protective against systemic fungal infection with *C. albicans*, but the protective efficacy can be inhibited by blocking antibodies. The invention provides an immunogenic composition comprising a glucan and a pharmaceutically acceptable carrier, characterized in that, when administered to a mammalian recipient, the composition elicits protective anti-glucan antibodies but does not elicit antibodies which inhibit the protective efficacy of the anti-glucan antibodies. The glucan may be presented on the surface of a protease-treated microbial cell or may be presented as a protein-glucan conjugate. The glucan may be substituted by a glucan mimotope, a peptidomimetic of a glucan mimotope, or nucleic acid encoding a mimotope. Anti-glucan-antibodies show broad spectrum microbicidal activity. β-glucans are preferred, particularly those containing one or more β-1,6 linkages.

21 Claims, 7 Drawing Sheets

OTHER PUBLICATIONS

Miura, et al., "Antigen-Specific Response of Murine Immune System Toward a Yeast Beta-Glucan Preparation, Zymosan," *FEMS Immunol Med Microbiol* 24:131-139 (1999).
Ohno, et al., "Solubilization of Yeast Cell-Wall Beta-(1-->3)-D-Glucan by Sodium Hypochlorite Oxidation and Dimethyl Sulfoxide Extraction," *Carbohydrate Res* 316:161-172 (1999).
Patent Abstracts of Japan, "Cosmetic" vol. 012, No. 312 (C-523), One Page (1988).
Ross, et al., "Therapeutic Intervention With Complement and Beta-Glucan in Cancer," *Immunopharmacology* 42(1-3):61-74 (1999).
Tokunaka, et al., "Immunopharmacological and Immunotoxicological Activities of a Water-Soluble (1->3)-Beta-D-Glucan, CSBG from Candidate spp," *Int J Immunopharm* 22(5):383-394 (2000).
Torres-Bauza, et al., "Protoplasts From Yeast and Mycelial Forms of *Candida albicans*," *J Gen Microbiol* 119:341-349 (1980).
Tzianabos, "Polysaccharide Immunomodulators as Therapeutic Agents: Structural Aspects and Biological Function," *Clinical Microbiology Reviews* 13(4):523-533 (2000).
Tzianabos, et al., "Protection Against Experimental Intraabdominal Sepsis by Two Polysaccharide Immunomodulators," *J Infect Dis* 178:200-206 (1998).
Bromuro et al., "Beta-glucan-CRM197 Conjugates as Candidates Antifugal Vaccines," *Vaccine* 2010, 28:2615-2623 (2010).
Pietrella et al., "A Beta-glucan-conjugate Vaccine and Anti-beta-glucan Antibodies are Effective Against Murine Vaginal Candidiasis as Assessed by a Novel in vivo Imaging Technique," *Vaccine* 2010, 28:1717-1725.
Casadevall, et al., "Antibody-Mediated Protection Through Cross-Reactivity Induces a Fungal Heresy Into Immunological Dogma," *Inf Immun* 75(11):5074-5078 (2007).
Honey, "β-Glucan Conjugate Provides Protection," *Nat Rev Immunol* 4:814 (2005).
Rachini, et al., "An Anti-B-Glucan Monoclonal Antibody Inhibits Growth and Capsule Formation of *Cryptococcus neoformans* In Vitro and Exerts Therapeutic, Anticryptococcal Activity In Vivo," *Inf Immun* 75(11):5085-5094 (2007).
Ross, et al., "Therapeutic Intervention With Complement and β-Glucan in Cancer," *Immunopharmacology* 42:61-74 (1999).
Sadamoto, et al., "Evidence for Interference by Immune Complexes in the Serodignosis of Cryptococcosis," *Microbiol Immunol* 37(2):129-133 (1993).
Tokunaka, et al., "Immunopharmacological and Immunotoxicological Activities of a Water-Soluble (1→3)-β-Glucan, CSBG From *Candida* spp," *Int J Immunopharm* 22:383-394 (2000).
Torosantucci, et al., "A Novel Glyco-Conjugate Vaccine Against Fungal Pathogens," *J Exp Med* 202(5):597-606 (2005).
Flavia De Bernardis, et al., "Intravaginal and Intranasal Immunizations Are Equally Effective in Inducing Vaginal Antibodies and Conferring Protection Against Vaginal Candidiasis," Infection and Immunity, 70(5):2725-2729 (2002).
Paul L. Fidel, et al., "Prospects for Development of a Vaccine to Prevent and Control Vaginal Candidiasis," Curr. Infect. Dis. Rep, 13:102-107 (2011).

FIGURE 3
—△— Adj-immunized
—○— Y-immunized
—◆— Y-DP-immunized
FIGURE 3A
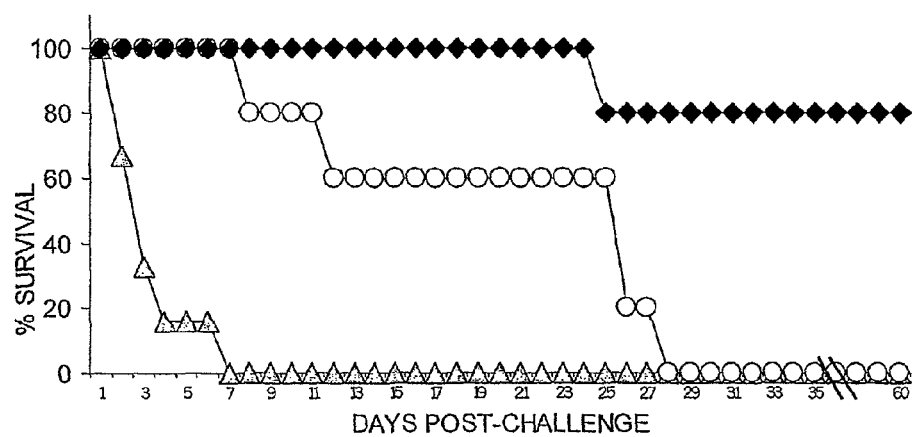
FIGURE 3B
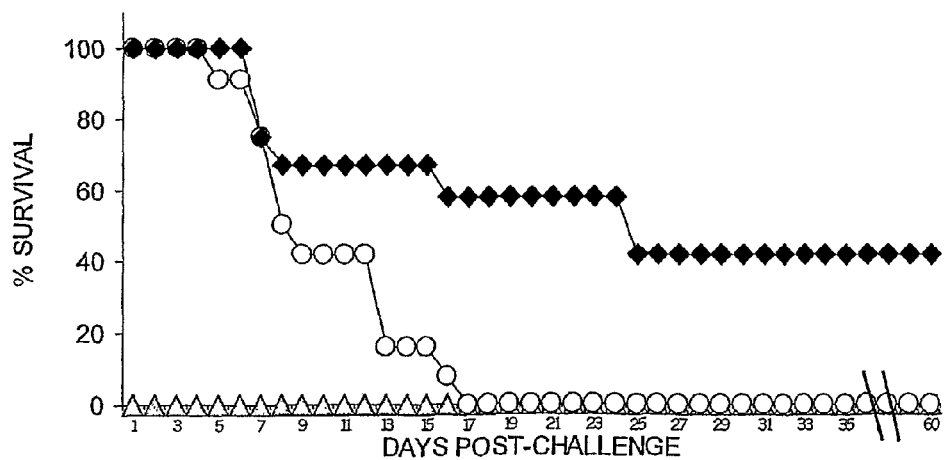

US 8,398,990 B2

GLUCAN-BASED VACCINES

CROSS-REFERENCE TO RELATED APPLICATIONS

This application is a continuation of U.S. application Ser. No. 11/701,250, filed Feb. 1, 2007, now U.S. Pat. No. 7,824, 688, which is a divisional of U.S. application Ser. No. 10/514, 483, filed May 26, 2005, now abandoned which is a 371 filing of PCT/IB03/02460, filed May 15, 2003, which claims priority to GB 0211118.5, filed May 15, 2002, from which applications priority is claimed pursuant to the provisions of 35 U.S.C. §§119/120, and which applications are hereby incorporated by reference in their entireties.

All documents cited herein are incorporated by reference in their entirety.

TECHNICAL FIELD

The invention relates to vaccines, more particularly those against fungal infections and disease.

BACKGROUND ART

Fungal infections are prevalent in several clinical settings, particularly in immunocompromised patients. The emergence of resistance to antimycotics, in particular to the azoles, has increased interest in therapeutic and prophylactic vaccination against these fungi [1]. Among fungal pathogens, *Candida albicans* is one of the most prevalent. This organism is one of the principal agents of widespread opportunistic infections in humans and causes candidiasis, a condition which is found in both normal and immunocompromised patients. There have been several attempts to provide anti-*Candida* vaccines.

There is widespread consensus in the field of medical mycology that cellular immunity is critical for successful host defence against fungi [2], although the potential efficacy of humoral immunity in protecting against two major fungal pathogens (*C. albicans* and *C. neoforzans*) has attracted attention [2,3]. For *C. neoformans*, antibodies to the capsular glucuronoxylomannan have been shown to mediate protection in animal models of infection. For *C. albicans*, cell-surface mannoproteins are the dominant antigenic components [1] of *C. albicans* and antibodies to mannan, proteases and a heat shock proteins have been associated with protection against infection. Other vaccine candidates include: members of the asparlyl proteinase (Sap2) family; the 65 kDa mannoprotein (MP65) [4]; adhesion molecules isolated from phosphomannan cell wall complexes [5]; peptides which mimic epitopes from the mannan portion of the phosphomannan complex of *Candida* [6]; and hemolysin-like proteins [7].

It is an object of the invention to provide further and better antigens for inducing protective and/or therapeutic immune responses against infections, particularly against fungal infections.

DISCLOSURE OF THE INVENTION

*Candida* cells contain all non-secreted candidate protective antigens but, even though they elicit high-level humoral and cell-mediated immune responses against various antigens, whole cell vaccines are ineffective. It has surprisingly been found that this low protective efficacy is not due to the absence of immune responses to particular antigens, but rather to the presence of blocking antibodies in animal serum which can interact with the intact fungus cell surface. In the absence of such blocking antibodies, anti-glucan antibodies have been found to be protective against systemic fungal infection, but the protective effect is inhibited when blocking antibodies are present. Fungal glucans are naturally poor immunogens and have not previously been considered for eliciting protection.

Thus the invention provides an immunogenic composition comprising a glucan and a pharmaceutically acceptable carrier wherein, when it is administered to a mammal, the composition elicits protective anti-glucan antibodies but does not elicit antibodies which inhibit the protective efficacy of the anti-glucan antibodies.

The Glucan

Glucans are glucose-containing polysaccharides found inter alia in fungal cell walls. α-glucans include one or more α-linkages between glucose subunits and β-glucans include one or more β-linkages between glucose subunits.

α-glucans are found in various organisms, including *S. mutans*, which has a cell wall containing both α-1,3- and α-1,6-glucans.

β-1,6-glucans occur frequently in fungi but are rarer outside fungi [8]. Within a typical fungal cell wall, β-1,3-glucan microfibrils are interwoven and crosslinked with chitin microfibrils to form the inner skeletal layer, whereas the outer layer consists of β-1,6-glucan and mannoproteins, linked to the inner layer via chitin and β-1,3-glucan. In *C. albicans*, 50-70% of the cell wall is composed of β-1,3- and β-1,6-glucans. *C. albicans* does not contain β-1-2-glucan(s) or β-1, 4-glucan(s). Full length native β-glucans are insoluble and are generally branched.

The glucan used in accordance with the invention may comprise α and/or β linkages. Where α linkages are present, the ratio of β linkages: α linkages in the glucan will typically be at least 2:1 (e.g. 3:1, 4:1, 5:1, 10:1, 20:1 or higher). In preferred embodiments, however, the glucan contains only β linkages.

β-glucans are preferred. The β-glucan may comprise one or more β-1,3-linkages and/or one or more β-1,6-linkages. It may also comprise one or more β-1,2-linkages and/or β-1,4-linkages. Particularly preferred are glucans containing one or more β-1,6-linkages.

The glucan may be branched.

Preferred glucans are β-glucans derived from the cell wall of a *Candida*, such as *C. albicans*. Other organisms from which β-glucans may be used include *Coccidioides immitis, Trichophyton verrucosum, Blastomyces dermatidis, Cryptococcus neoformans, Histoplasma capsulatum, Saccharomyces cerevisiae, Paracoccidioides brasiliensis*, and *Pythiumn insidiosum*.

Preferred glucans are fungal glucans i.e. glucans found in fungi. A 'fungal' glucan will generally be obtained from a fungus but, where a particular glucan structure is found in both fungi and non-fungi (e.g. in bacteria, lower plants or algae) then the non-fungal organism may be used as an alternative source.

Full-length native β-glucans are insoluble and have a molecular weight in the megadalton range. It is preferred to use soluble glucans in immunogenic compositions of the invention. Solubilisation may be achieved by fragmenting long insoluble glucans. This may be achieved by hydrolysis or, more conveniently, by digestion with a glucanase (e.g. with a β-1,3-glucanase or a β-1,6-glucanase). As an alternative, short glucans can be prepared synthetically by joining monosaccharide building blocks.

Low molecular weight glucans are preferred, particularly those with a molecular weight of less than 100 kDa (e.g. less than 80, 70, 60, 50, 40, 30, 25, 20, or 15 kDa). It is also possible to use oligosaccharides e.g. containing 60 or fewer (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units. Within this range, oligosaccharides with between 10 and 50 or between 20 and 40 monosaccharide units are preferred.

There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways. Reference 9, for instance, discloses a two-step procedure for preparing a water-soluble β-glucan extract from *Candida*, free from cell-wall mannan, involving NaClO oxidation and DMSO extraction. The resulting product ('*Candida* soluble β-D-glucan' or 'CSBG') is mainly composed of a linear β-1,3-glucan with a linear β-1,6-glucan moiety. Further methods for purifying β-glucans are disclosed in the examples herein, and 'glucan ghosts' comprise high-purity β-glucans. β-1,3-glucans are known for use as health supplements [10].

As disclosed in the examples, preferred glucans are those obtainable from *C. albicans*, especially (a) β-1,6-glucans with β-1,3-glucan lateral chains and an average degree of polymerisation of about 30, and (b) β-1,3-glucans with β-1, 6-glucan lateral chains and an average degree of polymerisation of about 4.

Pure β-glucans are, however, poor immunogens. For protective efficacy, therefore, β-glucans should be presented to the immune system in immunogenic form. This may be achieved in various ways. In two preferred embodiments of the invention, the β-glucan included in the composition of the invention is either: (a) a protease-treated and/or mannoprotein-depleted fungal cell which displays surface β-glucans; or (b) a glucan-carrier conjugate.

Protease-Treated Fungal Cells

β-glucans may be presented to the immune system on the surface of a fungal cell. As β-glucans are not normally exposed in sufficiently immunogenic form on the surface of fungal cells, however, the cells should be treated with protease (e.g. a non-specific protease, such as Proteinase K). Exposing fungi to protease in this way can deplete mannoprotein and remove molecules which elicit blocking antibodies.

Thus the invention provides a protease-treated fungal cell having surface-exposed β-glucans. Preferably, the fungal cell's cell wall is free or substantially free of mannoprotein.

The invention also provides an immunogenic composition comprising a fungal β-glucan and a pharmaceutically acceptable carrier, wherein the fungal β-glucan is a component of a protease-treated fungal cell. Preferably, the fungal cell's cell wall is free or substantially free of mannoprotein. More preferably, the composition as a whole is free or substantially free of mannoprotein.

The fungal cell is preferably a *Candida* and more preferably *C. albicans*.

Glucan-Carrier Conjugates

Glucans may be presented to the immune system in the form of glucan-carrier conjugates. The use of conjugation to carrier proteins in order to enhance the immunogenicity of carbohydrate antigens is well known [e.g. reviewed in refs. 11 to 19 etc.] and is used in particular for paediatric vaccines [20].

The invention provides a conjugate of (i) a carrier protein and (ii) a glucan. The glucan is preferably a β-glucan as defined above, and is more preferably a fungal β-glucan e.g. containing β-1,6 linkages.

The carrier protein may be covalently conjugated to the glucan directly, or a linker may be used.

Direct linkages to the protein may comprise oxidation of the glucan followed by reductive amination with the protein, as described in, for example, references 21 and 22.

Linkages via a linker group may be made using any known procedure, for example, the procedures described in references 23 and 24. A preferred type of linkage is an adipic acid linker, which may be formed by coupling a free —$NH_2$ group on an aminated glucan with adipic acid (using, for example, diimide activation), and then coupling a protein to the resulting saccharide-adipic acid intermediate [15, 25, 26]. Another preferred type of linkage is a carbonyl linker, which may be formed by reaction of a free hydroxyl group of a modified glucan with CDI [27, 28] followed by reaction with a protein to form a carbamate linkage. Other linkers include B-propionamido [29], nitrophenyl-ethylamine [30], haloacyl halides [31], glycosidic linkages [32], 6-aminocaproic acid [33], ADH [34], $C_4$ to $C_{12}$ moieties [35], etc.

Preferred carrier proteins are bacterial toxins or toxoids, such as diphtheria or tetanus toxoids. These are commonly used in conjugate vaccines. The $CRM_{197}$ diphtheria toxoid is particularly preferred [36]. Other suitable carrier proteins include the *N. meningitidis* outer membrane protein [37], synthetic peptides [38,39], heat shock proteins [40,41], pertussis proteins [42,43], protein D from *H. influenzae* [44], cytokines [45], lymphokines [45], hormones [45], growth factors [45], toxin A or B from *C. difficile* [46], iron-uptake proteins [47], etc. It is possible to use mixtures of carrier proteins.

A single carrier protein may carry multiple different glucans [48].

When the conjugate forms the glucan component in an immunogenic composition of the invention, the composition may also comprise free carrier protein [49].

After conjugation, free and conjugated glucans can be separated. There are many suitable methods e.g. hydrophobic chromatography, tangential ultrafiltration, diafiltration, etc. [see also refs. 50, 51 etc.]. Tangential flow ultrafiltration is preferred.

The glucan moiety in the conjugate preferably an low molecular weight glucan or an oligosaccharide, as defined above. Oligosaccharides will typically be sized prior to conjugation.

The protein-glucan conjugate is preferably soluble in water and/or in a physiological buffer.

Antibodies

The invention provides a composition comprising (1) antibody which recognises a glucan and (2) a pharmaceutically acceptable carrier. The glucan is preferably a β-glucan as defined above, and is more preferably a fungal β-glucan e.g. containing β-1,6 linkages.

The antibody is preferably a protective antibody, offering protection against microbial infection and/or disease. The microbe may be a fungus or a bacterium, examples of which are given below.

The composition is preferably free or substantially free from antibodies which inhibit the protective efficacy of the anti-glucan antibodies. For example, where the glucan is a fungal β-1,6-glucan then the composition is preferably free or substantially free from antibodies against non-glucan cell wall components, such as anti-mannoprotein antibodies.

The term 'antibody' includes any of the various natural and artificial antibodies and antibody-derived proteins which are available. Thus the term 'antibody' includes polyclonal antibodies, monoclonal antibodies, Fab fragments, F(ab')$_2$ fragments, Fv fragments, single-chain Fv (scFv) antibodies, oligobodies, etc.

Antibody-containing compositions of the invention may be used for passive immunisation.

To increase compatibility with the human immune system, it is preferred to use human antibodies. As an alternative, antibodies of the invention may be chimeric or humanized versions of non-human antibodies [e.g. refs. 52 & 53].

In chimeric antibodies, non-human constant regions are substituted by human constant regions but variable regions remain non-human.

Humanized antibodies may be achieved by a variety of methods including, for example: (1) grafting complementarity determining regions (CDRs) from the non-human variable region onto a human framework ("CDR-grafting"), with the optional additional transfer of one or more framework residues from the non-human antibody ("humanizing"); (2) transplanting entire non-human variable domains, but "cloaking" them with a human-like surface by replacement of surface residues ("veneering"). In the present invention, humanized antibodies include those obtained by CDR-grafting, humanizing, and veneering or variable regions. [e.g. refs. 54 to 60].

The constant regions of humanized antibodies are derived from human immunoglobulins. The heavy chain constant region can be selected from any of the five isotypes: α, δ, ε, γ or μ.

Humanized or fully-human antibodies can also be produced using transgenic animals that are engineered to contain human immunoglobulin loci. For example, ref. 61 discloses transgenic animals having a human Ig locus wherein the animals do not produce functional endogenous immunoglobulins due to the inactivation of endogenous heavy and light chain loci. Ref. 62 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. Ref. 63 discloses the use of the Cre/Lox system to modify the immunoglobulin locus in a mammal, such as to replace all or a portion of the constant or variable region to form a modified antibody molecule. Ref. 64 discloses non-human mammalian hosts having inactivated endogenous Ig loci and functional human Ig loci. Ref. 65 discloses methods of making transgenic mice in which the mice lack endogenous heavy chains, and express an exogenous immunoglobulin locus comprising one or more xenogeneic constant regions.

Antibodies of the invention may be produced by any suitable means (e.g. by recombinant expression).

Mimotopes

Antigenic carbohydrates can be mimicked by polypeptides ('mimotopes') [e.g. 6, 66, 67, 68]. The invention also provides a polypeptide comprising a mimotope of a glucan. The glucan is preferably a β-glucan as defined above, and is more preferably a fungal β-glucan e.g. containing β-1,6 linkages.

The mimotope preferably consists of at least 3 amino acids (e.g. at least 4, 5, 6, 7, 8, 9, 10, 11, 12, 13, 14, 15, 16, 17, 18, 19, 20, 25, 30 or more amino acids).

The polypeptide preferably consists of at least 3 amino acids (e.g. at least 4, 5, 6, 7, 8, 9, 10, 11, 12, 13, 14, 15, 16, 17, 18, 19, 20, 25, 30, 35, 40, 45, 50, 55, 60, 70, 80, 90, 100, 125, 150, 175, or at least 200 amino acids).

The polypeptide preferably consists of no more than 250 amino acids (e.g. no more than 225, 200, 190, 180, 170, 160, 150, 140, 130, 120, 110, 100, 95, 90, 80, 70, 60, 50, 45, 40, 35, 30, 25, 20, 19, 18, 17, 16, 15, 14, 13, 12, 11, 10, 9, 8, 7, 6 or even 5 amino acids).

Polypeptides consisting of between 6 and 20 amino acids are preferred.

Mimotopes of a glucan of interest may be identified in various ways. A preferred technique for identifying a mimotope involves display (e.g. phage display) of a library of polypeptide sequences followed by selection of polypeptides which bind to antibodies specific for the glucan of interest. The selection procedure may be iterative in order to focus on the best mimotopes.

Polypeptides of the invention may be prepared by various means.

A preferred method for production involves in vitro chemical synthesis [69, 70]. Solid-phase peptide synthesis is particularly preferred, such as methods based on t-Boc or Fmoc [71] chemistry. Enzymatic synthesis [72] may also be used in part or in full.

As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl-tRNA molecules) can be used to allow the introduction of D-amino acids or of other non-natural amino acids, such as iodo-Tyr or methyl-Phe, azidohomo-Ala, etc. [73].

To facilitate biological peptide synthesis, the invention provides nucleic acid that encodes a polypeptide of the invention. The nucleic acid may be DNA or RNA (or hybrids thereof), or their analogues, such as those containing modified backbones (e.g. phosphorothioates) or peptide nucleic acids (PNA). It may be single-stranded (e.g. mRNA) or double-stranded, and the invention includes both individual strands of a double-stranded nucleic acid (e.g. for antisense, priming or probing purposes). It may be linear or circular. It may be labelled. It may be attached to a solid support.

Nucleic acid according to the invention can, of course, be prepared in many ways e.g. by chemical synthesis (e.g. phosphoramidite synthesis of DNA) in whole or in part, by nuclease digestion of longer molecules, from genomic or cDNA libraries, by the use of polymerases etc.

The invention provides vectors (e.g. plasmids) comprising nucleic acid of the invention (e.g. expression vectors and cloning vectors) and host cells (prokaryotic or eukaryotic) transformed with such vectors.

These vectors can also be used for nucleic acid immunisation [e.g. refs. 74 to 85 etc.]. Peptides can be expressed in vivo in this way, as can therapeutic antibodies. DNA vaccination for the in vivo expression of polypeptide mimotopes of carbohydrate antigens is known [e.g. 86].

Host cells which contain nucleic acid of the invention and which express polypeptides or antibodies of the invention may be used as delivery vehicles e.g. commensal bacteria [87]. This is particularly useful for delivery to mucosal surfaces.

Mimotopes may be useful immunogens in their own right. However, they may be refined to improve immunogenicity or to improve pharmacologically important features such as bioavailability, toxicology, metabolism, pharmacokinetics, etc. Mimotopes of the invention can be used for designing peptidomimetic molecules [e.g. refs. 88 to 93] with immunogenic. These will typically be isosteric with respect to the mimotopes of the invention but will lack one or more of their peptide bonds. For example, the peptide backbone may be replaced by a non-peptide backbone while retaining important amino acid side chains.

Medical Treatments and Uses

Pharmaceutical compositions of the invention may comprise (a) a glucan (e.g. in the form of a protease-treated cell or a carrier-glucan conjugate), an anti-glucan antibody, a polypeptide comprising a mimotope of a glucan, a peptidomimetic of the mimotope, and/or a nucleic acid vector encoding the mimotope, and (b) a pharmaceutically acceptable carrier.

The invention provides a glucan, an anti-glucan antibody, a mimotope of a glucan, a peptidomimetic of the mimotope, and/or a nucleic acid vector encoding the mimotope, for use as a medicament.

The invention also provides a method for raising an antibody response in a mammal, comprising administering a pharmaceutical composition of the invention to the mammal. The antibody response is preferably an IgA or IgG response.

The invention also provides a method for treating a mammal suffering from a microbial infection, comprising administering to the patient a pharmaceutical composition of the invention. The infection disease may be systemic or mucosal.

The invention also provides a method for protecting a mammal against a microbial infection, comprising administering to the mammal a pharmaceutical composition of the invention.

The invention also provides the use of a glucan, an anti-glucan antibody, a mimotope of a glucan, a peptidomimetic of the mimotope, and/or a nucleic acid vector encoding the mimotope, in the manufacture of a medicament for preventing or treating a microbial infection in a mammal.

The mammal is preferably a human. The human may be an adult or, preferably, a child. The human may be immunocompromised.

The invention may utilise both (i) an immunogen (e.g. a glucan, a glucan mimotope, a peptidomimetic of the mimotope and/or a nucleic acid vector encoding the mimotope), and (ii) an anti-glucan antibody or nucleic acid encoding the antibody, in order to provide active and passive immunisation at the same time. These may be administered separately or in combination. When administered separately, they will typically be administered within 7 days of each other. They may be packaged together in a kit.

Because glucans (and β-glucans in particular) are an essential and principal polysaccharide constituent of almost all pathogenic fungi, particularly those involved in infections in immunocompromised subjects, and also in bacterial pathogens and protozoa, anti-glucan immunity may have efficacy against a broad range of pathogens and diseases. For example, anti-glucan serum raised after immunisation with *S. cerevisiae* is cross-reactive with *C. albicans*. Broad spectrum immunity is particularly useful because, for these human infectious fungal agents, chemotherapy is scanty, antifungal drug resistance is emerging and the need for preventative and therapeutic vaccines is increasingly recognized.

The uses and methods of the invention are particularly useful for treating/protecting against infections of: *Candida* species, such as *C. albicans*; *Cryptococcus* species, such as *C. neoformans*; *Enterococcus* species, such as *E. faecalis*; *Streptococcus* species, such as *S. pneumoniae, S. mutans, S. agalactiae* and *S. pyogenes*; *Leishmania* species, such as *L. major*; *Acanthamoeba* species, such as *A. castellani*; *Aspergillus* species, such as *A. fumigatus* and *A. flavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. immitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythiumn* species such as *P. insidiosum*; and *Escherichia* species, such as *E. coli*.

The uses and methods are particularly useful for preventing/treating diseases including, but not limited to: candidosis, aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, cystic fibrosis, typhoid fever, gastroenteritis and hemolytic-uremic syndrome. Anti-*C. albicans* activity is particularly useful for treating infections in AIDS patients.

Efficacy of therapeutic treatment can be tested by monitoring microbial infection after administration of the composition of the invention. Efficacy of prophylactic treatment can be tested by monitoring immune responses against β-glucan (e.g. anti-β-glucan antibodies) after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, ocular, nasal, aural, or pulmonary administration. Injection or intranasal administration is preferred.

The invention may be used to elicit systemic and/or mucosal immunity.

Dosage treatment can be a single dose schedule or a multiple dose schedule.

The Pharmaceutically Acceptable Carrier

The pharmaceutically acceptable carrier can be any substance that does not itself induce the production of antibodies harmful to the patient receiving the composition, and which can be administered without undue toxicity. Suitable carriers can be large, slowly-metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Liposomes are suitable carriers. A thorough discussion of pharmaceutical carriers is available in ref. 94.

Microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 95]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

The invention also provides a delivery device containing a pharmaceutical composition of the invention. The device may be, for example, a syringe or an inhaler.

Immunogenic Compositions

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Even though β-glucans are themselves adjuvants, the immunogenic composition may include a further adjuvant. Preferred adjuvants to enhance effectiveness of the composition include, but are not limited to: (A) aluminium compounds (e.g. aluminium hydroxide, aluminium phosphate, aluminium hydroxyphosphate, oxyhydroxide, orthophosphate, sulphate, etc. [e.g. see chapters 8 & 9 of ref. 96]), or mixtures of different aluminium compounds, with the compounds taking any suitable form (e.g. gel, crystalline, amorphous, etc.), and with adsorption being preferred; (B) MF59 (5% Squalene, 0.5% Tween 80, and 0.5% Span 85, formulated into submicron particles using a microfluidizer) [see Chapter 10 of ref. 96; see also ref. 97]; (C) liposomes [see Chapters 13 and 14 of ref. 96]; (D) ISCOMs [see Chapter 23 of ref. 96], which may be devoid of additional detergent [98]; (E) SAF, containing 10% Squalane, 0.4% Tween 80, 5% pluronic-block polymer L121, and thr-MDP, either microfluidized into a submicron emulsion or vortexed to generate a larger particle size emulsion [see Chapter 12 of ref. 96]; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 [see Chapter 22 of ref. 96], also known as Stimulon™; (H) chitosan [e.g. 99]; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. [see Chapters 27 & 28 of ref. 96]; (K) microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid) such as poly(lactide-co-glycolide), a polyhydroxybutyric acid, a polyorthoester, a polyanhydride, a polycaprolactone, etc.); (L) monophosphoryl lipid A (MPL) or 3-O-deacylated MPL (3dMPL) [e.g. chapter 21 of ref. 96]; (M) combinations of 3dMPL with, for example, QS21 and/or oil-in-water emulsions [100]; (N) oligonucleotides comprising CpG motifs [101] i.e. containing at least one CG dinucleotide, with 5-methylcytosine optionally being used in place of cytosine; (O) a polyoxyethylene ether or a polyoxyethylene ester [102]; (P) a polyoxyethylene sorbitan ester surfactant in combination with an octoxynol [103] or a polyoxyethylene alkyl ether or ester surfactant in combination with at least one additional non-ionic surfactant such as an octoxynol [104]; (O) an immunostimulatory oligonucleotide (e.g. a CpG oligonucleotide) and a saponin [105]; (R) an immunostimulant and a particle of metal salt [106]; (S) a saponin and an oil-in-water emulsion [107]; (T) a saponin (e.g. QS21)+3dMPL+IL-12 (optionally+a sterol) [108]; (U) *E. coli* heat-labile enterotoxin ("LT"), or detoxified mutants thereof, such as the K63 or R72 mutants [e.g. Chapter 5 of ref. 109]; (V) cholera toxin ("CT"), or detoxified mutants thereof [e.g. Chapter 5 of ref. 109]; (W) double-stranded RNA; (X) monophosphoryl lipid A mimics, such as aminoalkyl glucosaminide phosphate derivatives e.g. RC-529 [110]; (Y) polyphosphazene (PCPP); or (Z) a bioadhesive [111] such as esterified hyaluronic acid microspheres or a mucoadhesive selected from the group consisting of cross-linked derivatives of poly(acrylic acid), polyvinyl alcohol, polyvinyl pyrollidone, polysaccharides and carboxymethylcellulose. Other substances that act as immunostimulating agents to enhance the effectiveness of the composition [e.g. see Chapter 7 of ref. 96] may also be used. Aluminium salts (especially aluminium phosphates and/or hydroxides) are preferred adjuvants for parenteral immunisation. Mutant toxins are preferred mucosal adjuvants.

Muramyl peptides include N-acetyl-muramyl-L-threonyl-D-isoglutamine(thr-MDP), N-acetyl-normuramyl-L-alanyl-D-isoglutamine (nor-MDP), N-acetylmurarnyl-L-alanyl-D-isoglutaminyl-L-alanine-2-(1'-2'-dipalmitoyl-sn-glycero-3-hydroxyphosphoryloxy)-ethylamine MTP-PE), etc.

Once formulated, the compositions of the invention can be administered directly to the subject. The subjects to be treated can be animals; in particular, human subjects can be treated. The vaccines are particularly useful for vaccinating children and teenagers.

Immunogenic compositions of the invention may be used therapeutically (i.e. to treat an existing infection) or prophylactically (i.e. to prevent future infection). Therapeutic immunisation is particularly useful for treating *Candida* infection in immunocompromised subjects.

As well as β-glucan, the composition may comprise further antigenic components. For instance, the composition may include one or more further saccharides. For instance, the composition may comprise saccharides from serogroups A, C, W135 and/or Y of *Neisseria meningitidis*. These will typically be conjugated to carrier proteins, and saccharides from different serogroups of *N. meningitidis* may be conjugated to the same or different carrier proteins. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Improved immunogenicity of the MenA component has been observed when it is present in excess (mass/dose) to the MenC component.

The composition may also comprise protein antigens.

Antigens which can be included in the composition of the invention include:

antigens from *Helicobacter pylori* such as CagA [113 to 116], VacA [117, 118], NAP [119, 120, 121], HopX [e.g. 122], HopY [e.g. 122] and/or urease.

a protein antigen from *N. meningitidis* serogroup B, such as those in refs. 123 to 129, with protein '287' (see below) and derivatives (e.g. 'ΔG287') being particularly preferred.

an outer-membrane vesicle (OMV) preparation from *N. meningitidis* serogroup B, such as those disclosed in refs. 130, 131, 132, 133, etc.

a saccharide antigen from *N. meningitidis* serogroup C, such as the oligosaccharide disclosed in ref. 134 from serogroup C [see also ref. 135].

a saccharide antigen from *Streptococcus pneumoniae* [e.g. 136, 137, 138].

an antigen from hepatitis A virus, such as inactivated virus [e.g. 139, 140].

an antigen from hepatitis B virus, such as the surface and/or core antigens [e.g. 140, 141].

an antigen from hepatitis C virus [e.g. 142].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 143 & 144].

a diphtheria antigen, such as a diphtheria toxoid [e.g. chapter 3 of ref. 145] e.g. the $CRM_{197}$ mutant [e.g. 146].

a tetanus antigen, such as a tetanus toxoid [e.g. chapter 4 of ref. 145].

a saccharide antigen from *Haemophilus influenzae* B [e.g. 135].

an antigen from *N. gonorrhoeae* [e.g. 123, 124, 125].

an antigen from *Chlamydia pneumoniae* [e.g. 147, 148, 149, 150, 151, 152, 153].

an antigen from *Chlamydia trachomatis* [e.g. 154].

an antigen from *Porphyromonas gingivalis* [e.g. 155].

polio antigen(s) [e.g. 156, 157] such as IPV or OPV.

rabies antigen(s) [e.g. 158] such as lyophilised inactivated virus [e.g. 159, RabAvert™].

measles, mumps and/or rubella antigens [e.g. chapters 9, 10 & 11 of ref. 145].

antigen(s) from influenza virus [e.g. chapter 19 of ref. 145], such as the haemagglutinin and/or neuraminidase surface proteins antigen(s) from a paarmyxovirus such as respiratory syncytial virus (RSV [160, 161]) and/or parainfluenza virus (PIV3 [162]).

an antigen from *Moraxella catarrhalis* [e.g. 163].

an antigen from *Streptococcus agalactiae* (group B streptococcus) [e.g. 164, 165].

an antigen from *Streptococcus pyogenes* (group A streptococcus) [e.g. 165, 166, 167].

an antigen from *Staphylococcus aureus* [e.g. 168].

an antigen from *Bacillus anthracis* [e.g. 169, 170, 171].

an antigen from a virus in the flaviviridae family (genus flavivirus), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

The composition may comprise one or more of these further antigens.

Toxic protein antigens may be detoxified where necessary (e.g. detoxification of pertussis toxin by chemical and/or genetic means [144]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens are preferably adsorbed to an aluminium salt.

Antigens in the composition will typically be present at a concentration of at least 1 μg/ml each. In general, the concentration of any given antigen will be sufficient to elicit an immune response against that antigen.

As an alternative to using proteins antigens in the composition of the invention, nucleic acid encoding the antigen may be used. Protein components of the compositions of the invention may thus be replaced by nucleic acid (preferably DNA e.g. in the form of a plasmid) that encodes the protein.

Compositions of the invention may be used in conjunction with anti-fungals, particularly where a patient is already infected. The anti-fungal offers an immediate therapeutic effect whereas the immunogenic composition offers a longer-lasting effect. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref. 172]. The anti-fungal and the immunogenic composition may be administered separately or in combination. When administered separately, they will typically be administered within 7 days of each other. After the first administration of an immunogenic composition, the anti-fungal may be administered more than once.

DEFINITIONS

The term "comprising" means "including" as well as "consisting" e.g. a composition "comprising" X may consist exclusively of X or may include something additional e.g. X+Y.

BRIEF DESCRIPTION OF DRAWINGS

FIG. 3 shows the results of lethal challenge experiments. FIGS. 3A and 3B show surviving animals after challenge.

FIGS. 8 and 10 are SDS-PAGE gels of the conjugate (8) before and (10) after ultrafiltration. FIGS. 9 and 11 are immunoblots of the conjugate (9) before and (11) after ultrafiltration.

MODES FOR CARRYING OUT THE INVENTION

Preparation of Mannoprotein-Depleted Yeast Cells

*C. albicans* strain BP, serotype A, from the type collection of the Istituto Superiore di Sanità (Rome, Italy), was routinely maintained on Sabouraud agar slants. For all experiments, fungus was cultured in the yeast form in liquid Winge medium at 28° C., washed twice in saline, counted in a haemocytometerer, and resuspended at the desired concentration in sterile saline.

For the preparation of normal cells ('Y cells') yeast cells suspensions ($10^8$ cells/ml) were inactivated at 80° C. for 30 min, washed and stored at 4° C. for no more than a week.

To prepare mannoprotein-depleted cells ('YDP cells'), heat-inactivated Y cells as above ($10^8$/ml) were treated with 50 mM DTT in 5 mM EDTANa$_2$ (1 hour, 37° C.). 500 µg/ml Proteinase K (Sigma) was added to the digestion mixture and the cells were treated for one further hour at 37° C. The fungal cells were extensively washed with saline to remove enzyme, resuspended in saline and used immediately after.

Germ-tube (GT) or hyphal forms of *C. albicans* were obtained by culturing cells in Lee's medium at 37° C.

Immunisation with Y Cells or YDP Cells

Female, 4 weeks old CD2F1 and SCID mice (Charles River Laboratory, Calco, Italy) were immunised with Y- or YDP-cells. Mice were subcutaneously injected twice, at weekly intervals, with Y- or YDP-cells ($10^6$ cells/100 µl/mouse) in complete Freund's adjuvant (Sigma), and five times by the intraperitoneal route with the same number of immunising cells without adjuvant. Control animals were injected with Freund's adjuvant and saline only.

Analysis of the Immune Response

Y-cells contain all of the antigenic cell wall and cytoplasmic constituents of *C. albicans* and so they should be able to immunise mice against all such antigens. Due to protease treatment, however, YDP-cells should not be able to induce a consistent immune reaction against cell-surface constituents.

To assess antibody responses, immunised animals were bled by retroorbital puncture and sera pooled from each immunisation group were examined for antibody content by immunofluorescence assays. Y— or YDP-cells were spotted onto microscope slides and reacted with various dilution of murine anti-Y or anti-YDP sera or with monoclonal antibody AF1 (specific for a β-1,2-mannooligosaccharidic epitope which is highly-expressed on the surface of *C. albicans* yeast cells) in 0.01M PBS. After extensive washings, slides were treated with FITC-conjugated anti-mouse IgM antibody and observed with a Leitz Diaplan fluorescence microscope.

Figure 1:
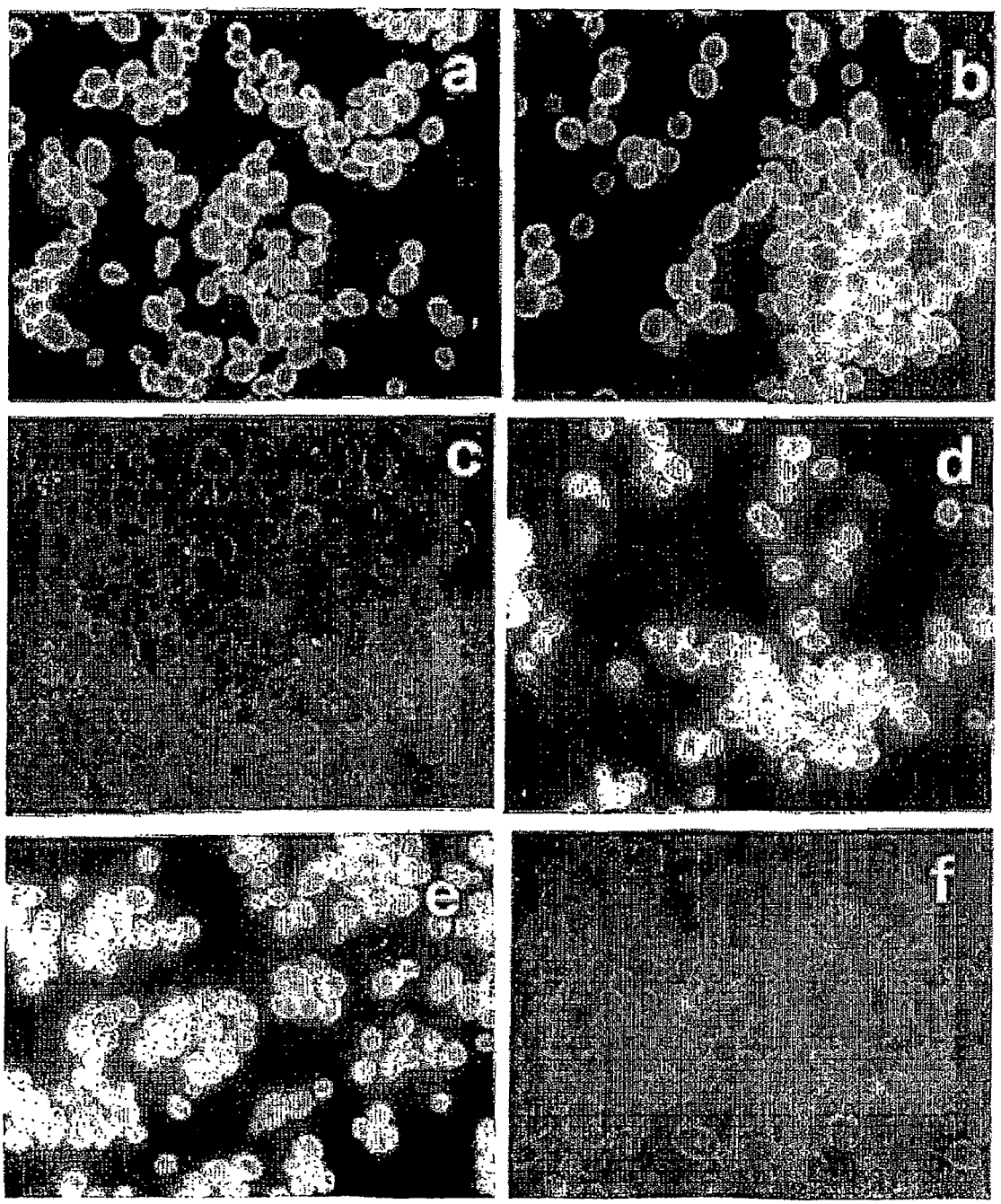
FIG. 1 shows immunofluorescence data. The cells are either untreated fungal 'Y' cells (1A, 1C, 1E) or proteinase-treated 'YDP' cells (1B, 1D, 1F). The labelling antibody is anti-Y-serum 1B), anti-YDP-serum (1C, 1D) or anti-mannoprotein antibody AF 1 (1E, 1F).

Anti-YDP serum was strongly reactive in immunofluorescence with YDP-cells (FIG. 1B) but very poorly so with Y-cells (FIG. 1D). Conversely, anti-mannoprotein antibody AF1 reacted with Y-cells (FIG. 1E) but not with YDP-cells (FIG. 1F). The surface profile of YDP-cells is thus very different from that of Y-cells.

Sera were also analysed by ELISA. Polystyrene microtitre plates were coated with antigens at 50 µg/ml in carbonate buffer, pH 9.6. Plates were blocked with 3% skim milk in phosphate-buffered saline (PBS), reacted with two-fold dilutions of mouse sera in PBS-0.05%-Tween 20 and developed with alkaline phosphatase-conjugated rabbit anti-mouse IgG or IgM as the secondary antibody and p-nitrophenyl phosphate disodium as the enzyme substrate. Pooled sera from adjuvant-immunized mice were used as negative control. Plates were read at 405 nm and antibody titres were defined as the highest dilution of mouse sera that gave an OD reading at least twice that of the negative control.

Seven antigens were used:
- *C. albicans* Y cells ($10^6$/well);
- *C. albicans* germ-tube cells ($10^6$/well);
- laminarin (β-1,3-glucan, Sigma)
- pustulan (β-1,6-glucan, CalbioChem);
- fungal mannoprotein ('Secr-MP'), prepared from the supernatant of a 24 hour fungal culture in Lee's medium at 28° C.;
- mannoprotein fraction MP-F2, purified from the *C. albicans* cell wall; and
- *C. albicans* soluble glucan antigens (GG-zym), obtained by (i) preparing glucan ghosts by repeated hot alkali-acid extractions of fungal cell walls to give purified β-1,3- and glucans and (ii) digesting the ghosts with β-1,3-glucanase (Zymoliase 100T, Seikagaku) for 1 hour at 37° C.

Results were as follows, with values being from one representative experiment out of three performed with similar results:

| Antigen | Antibody titres ($\times 10^3$) | |
|---|---|---|
| | Anti-Y serum | anti-YDP serum |
| Y cells | 1.28 | 40 |
| Germ-tubes | 1.28 | 40 |
| β-1,3-glucan | 2.56 | 2.56 |
| β-1,6-glucan | 2.56 | 1.28 |
| Secr-MP | 2.56 | 80 |
| MP-F2 | >2.56 | 320 |
| GG-Zym | 2.56 | 2.56 |

Thus anti-Y-cell serum contained antibodies against all major cell wall constituents present in both Y and GT forms, including β-1-6 and β-1-3 glucans, as well as against major cytoplasmic antigens.

In contrast, and confirming expectations, anti-YDP-cell serum had an elevated titre of anti-glucan antibodies but low antibody titres against the whole yeast or germ-tube cells, as well as cell surface-located or secretory mannoprotein.

To assay the induction of cell-mediated immunity following Y- or YDP-cell immunisation, spleen cells of control or immunised mice were induced to proliferate in vitro in the presence of Y- or YDP-cells, as well as with the β-glucan preparation.

Briefly, splenocyte suspension in 3 ml of 0.16 M Tris-buffered NH$_4$Cl, pH 7.2, were added with 9 ml of complete medium (RPMI 1640, supplemented with 5% foetal calf serum, 100 U/ml penicillin, 100 mg/ml streptomycin, 1 mM sodium piruvate, 2 mM L-glutamine, MEM-non essential aminoacids, $10^{-5}$ M 2-mercaptoethanol). Splenocytes were washed by centrifugation, plated in multiwell plates ($10^6$/ml, 200 ml/well) and stimulated with Y- or YDP-cells ($10^5$/well), with the GG-zym fraction (50 mg/ml) or with Concanavalin A (2 mg/ml=control). Each condition was assayed in triplicate. Splenocyte cultures were incubated at 37° C. in a 5% CO$_2$ atmosphere. Proliferation was evaluated as $^3$H-thymidine incorporation after 4 days for the antigenic stimuli and after 2 days of incubation for the polyclonal control stimulant. Stimulation indexes were calculated by dividing mean c.p.m. values of stimulated splenocyte cultures with those of unstimulated control cultures.

Figure 2:
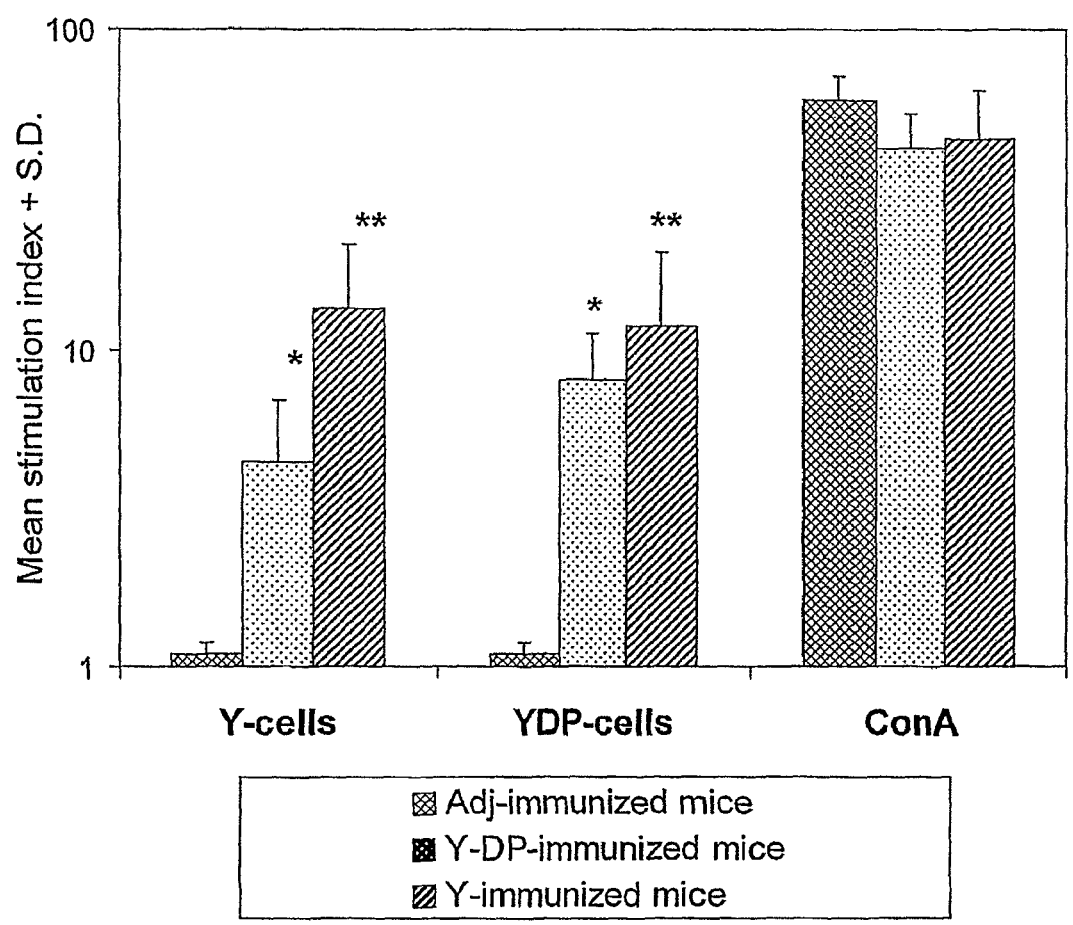
FIG. 2 shows mean stimulation index values (±SD) measured experimental groups with respect to unstimulated control cultures. Asterisks indicate a significant difference versus the controls (*$p<0.05$ or **$p<0.001$, as assessed by ANOVA and Bonferroni's multiple t test). All other differences in proliferative response were not significant.

As shown in FIG. 2, immunisation with Y- or YDP-cells were largely cross-reactive in stimulating a consistent degree of splenocyte proliferation, although a more intense response was seen with splenocytes stimulated in vitro with the specific immunising antigenic preparation. The splenocytes of all animals, including the non-immunised controls, responded to the polyclonal stimulation with ConA. No proliferation was detected in splenocyte cultures stimulated in vitro with β-glucan of *C. albicans*.

Overall, therefore, immunisation with Y- or YDP-cells induced largely cross-reactive humoral and CMI responses to antigens present on both cellular preparations. However, anti-MP and anti-Y-cell surface directed antibodies were present only in mice immunised with whole Y cells.

Protection Against Lethal Challenge

Having demonstrated that immunisation with Y cells induced consistent humoral and cell-mediated immune responses against major antigenic constituents of the fungus, the protective capacity of cells was tested in an acutely lethal mouse candidiasis model.

Protection was evaluated by monitoring animal survival (15 per group) for 60 days after intravenous challenge with a lethal dose of *C. albicans*. The dose was either $1 \times 10^6$ (FIG. 3A) or $2 \times 10^6$ (FIG. 3B) cell in 0.1 ml, or an adjuvant-only control.

Mice in the non-immunised control group had a median survival time of 1-2 days at the higher dose (FIG. 3B). Mice immunised with Y-cells showed an increased median survival time to the fungal challenge but had all died by day 15-17 after challenge and overall survival rates were not statistically different from the controls.

In contrast, animals immunised with YDP cells were much more resistant, with median survival >60 days. Differences in survival rates of YDP-immunized animals compared to adjuvant-treated animals and to Y-cell immunised animals were statistically significant (p<0.05, Fisher exact test) at both doses.

Protection was also evaluated by quantifying the extent of *Candida* outgrowth in the kidneys of animals infected with $10^6$ cells. This involved aseptic removal of the left kidney of sacrificed mice at day 7 post-challenge followed by homogenisation in sterile saline containing 0.1% Triton-X100 (Sigma). The number of colony forming units (CFU) per organ was determined by a plate dilution method on Sabouraud dextrose agar. Each kidney was examined separately and at least three distinct dilution from each sample were assayed in triplicate.

Figure 3C:
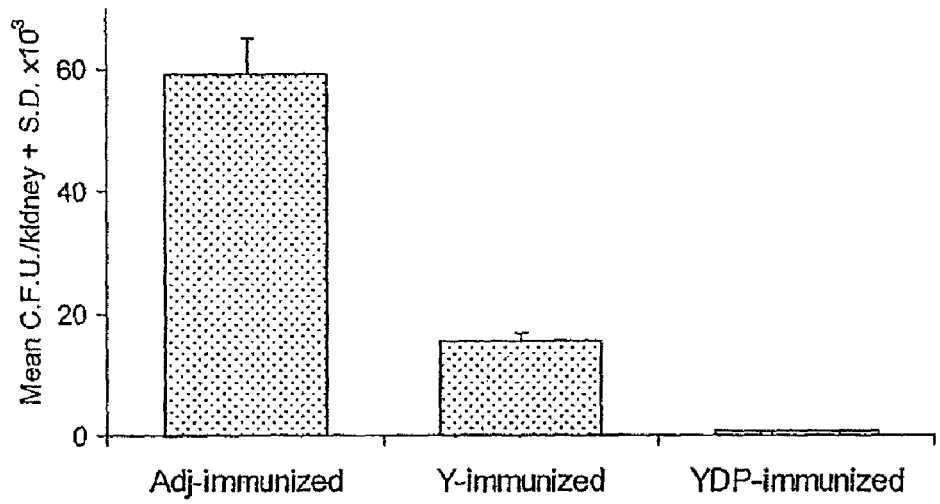
FIG. 3C shows kidney infection data.

As shown in FIG. 3C, mean fungus burden in the kidney was much lower in the YDP-cell immunised mice (CFU $<10^3$) than in the Y-cell immunised group ($15.4\pm0.6\times10^3$; p<0.05 by Kruskal-Wallis ANOVA and Bonferroni-type non parametric multiple comparison) and in the control group ($\sim60\times10^3$; p<0.05). The difference between the Y-cell and control groups was not statistically significant.

Experiments were also performed with SCID mice with the same schedule of vaccination as for immunocompetent animals. No protection was observed, demonstrating that adaptive immune responses are essential for protection. Unlike the reports in reference 173 for *C. neoformans*, therefore, CD4$^+$ cells are not involved in the antibody-mediated protection.

Passive Immunisation

As a major difference in the immune response to Y- or YDP-cells was in the antibody specificities to cell wall constituents, the ability of immune sera to transfer protection to non-immune animals was tested. These experiments also evaluated the potential contribution of the immune system of the recipient mice to the protection conferred by the passively-administered serum.

CD2F1 or SCID mice were passively immunised by a single intraperitoneal injection of 0.5 ml of anti-Y— or anti-YDP-cell serum. Control animals received serum from adjuvant-immunised mice. Each serum was heat-treated (56° C., 30 min) before transfer to inactivate heat-labile, non-antibody constituents. Mice were intravenously challenged two hours after transfer of sera with a sublethal dose of *C. albicans* ($5\times10^5$ cells) and protection was evaluated two days later using the kidney model as described above. These experiments were performed by using various batches of serum from animals independently immunised with the YDP- or Y-cell vaccine.

Results at 2 days post-challenge were as follows, with data representing weighted means of individual CFU counts enumerated from each group of mice. Statistical analysis was by Kruskal-Wallis ANOVA followed by non-parametric Bonferroni-type multiple comparison test:

| Recipient mouse | Pre-challenge treatment | Kidney fungal burden (CFU $\times 10^{-3} \pm$ SD) | p | |
|---|---|---|---|---|
| CD2F1 | Control (Adjuvant only) serum | 361.7 ± 17.6 | — | |
|  | anti-Y-cell serum 1 | 393.8 ± 7.7 | n.s. | <0.01 |
|  | anti-YDP-cell serum 1 | 8.7 ± 0.4 | <0.05 | |
| SCID | Control (Adjuvant only) serum | 214.4 ± 1.8 | — | |
|  | anti-Y-cell serum 2 | 392.2 ± 7.7 | n.s. | <0.05 |
|  | anti-YDP-cell serum 2 | 44.2 ± 0.8 | 0.05 | | n.s. = not significant

Thus animals receiving anti-Y-cell serum had the same elevated fungus burden in their kidney as those receiving the control non-immune serum. In contrast, those receiving the anti-YDP cell serum had significantly fewer fungal cells in their kidney than the animals receiving control serum. This was observed with different batches of respective immune sera, and in both the immunocompetent and the SCID mice.

As these data suggested that antibodies play a significant role in protection, the IgM fraction of serum from the YDP-immunised mice was purified and used for passive immunisation. The same fraction purified from the serum of animals given adjuvant only was used as a control. In a single experiment, the fungus kidney burden on day 2 post-challenge of four mice intravenously injected $10^6$ cells of *C. albicans* was $290\pm8$ ($\times10^3$) cells against $1359\pm18$ ($\times10^3$) cells in the kidney of control mice (p<0.01). The IgM fraction of YDP serum was highly reactive against glucan extract of *C. albicans*.

Removal of Passive Immunisation Efficacy

Serum antibodies generated by immunisation with YDP-cells recognize β-glucan constituents (see above). These antibodies were removed and passive transfer of immunity was re-tested.

Anti-Y or anti-YDP-cell sera were selectively adsorbed to remove glucan-specific or anti-surface mannoproteins antibodies. Sera (2 ml) were treated (1 hour, 0° C.) with 10 mg of particulate glucan (glucan ghosts) or with $2 \times 10^8$ live yeast cells of C. albicans. Adsorbants were removed by centrifugation, and the procedure was repeated three times. Efficacy of the adsorption procedure was evaluated by ELISA, using yeast cells or GG-zym as the coating antigens.

This procedure typically lowered the anti-β-glucan titres of anti-YDP sera and the anti-MP titre of anti-Y sera by 2 to 3 logs. Antibodies against β-glucan were not removed by adsorption with intact Y cells.

Figure 4:
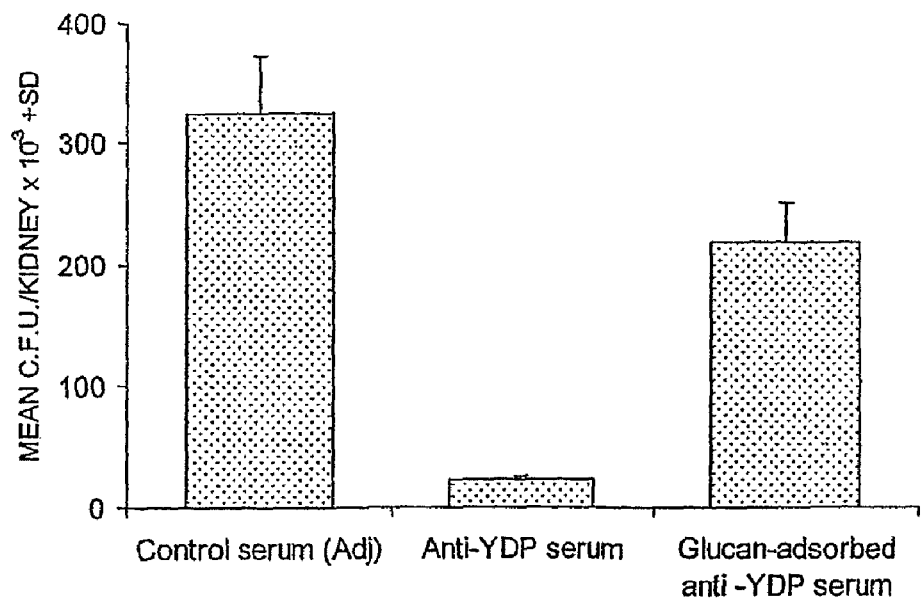
FIGS. 4 and 5 show the effect of pre-adsorption of sera on passive immune transfer.

The effect of pre-adsorption on YDP-sera was also assessed in the kidney burden model (FIG. 4). Unadsorbed or pre-adsorbed sera (0.5 ml/mouse) were given i.p. to mice (three per group) two hours before an intravenous sublethal challenge with C. albicans ($5 \times 10^5$ cells/mouse). Kidney invasion was assessed 48 hours post-challenge by individual CFU counts.

YDP-serum was much better ($p<0.05$) than the control serum, but pre-adsorption with β-glucans removed this effect ($p<0.05$), with no statistically significant different between control serum and adsorbed-serum.

Therefore an appreciable level of protection can be transferred to naive animals by the serum of YDP-cell recipient animals, the protective serum factor is heat-stable, and the immunoglobulin fraction of the serum is also protective. The protective serum is rich in anti-β-glucan antibodies and poor in anti-MP antibodies. When adsorbed on pure β-glucan, the serum loses much of its protective capacity. Moreover, the anti-Y-cell serum was protective when the anti-mannoprotein but not the anti-β-glucan antibodies were lost. Overall, this evidence suggests that protective IgM include those recognizing β-glucan.

Protective and Non-Protective Antagonistic Antibodies

The previous data suggest that anti-β-glucan antibodies play a role in the protection conferred by the YDP-cell vaccine. However, the sera of animals immunised with the Y-vaccine also contain high titres of anti-β-glucan antibodies (see above). Thus the Y-sera may contain a substance, not present in the YDP-sera, which inhibits the activity of the anti-β-glucan antibodies.

Figure 5:
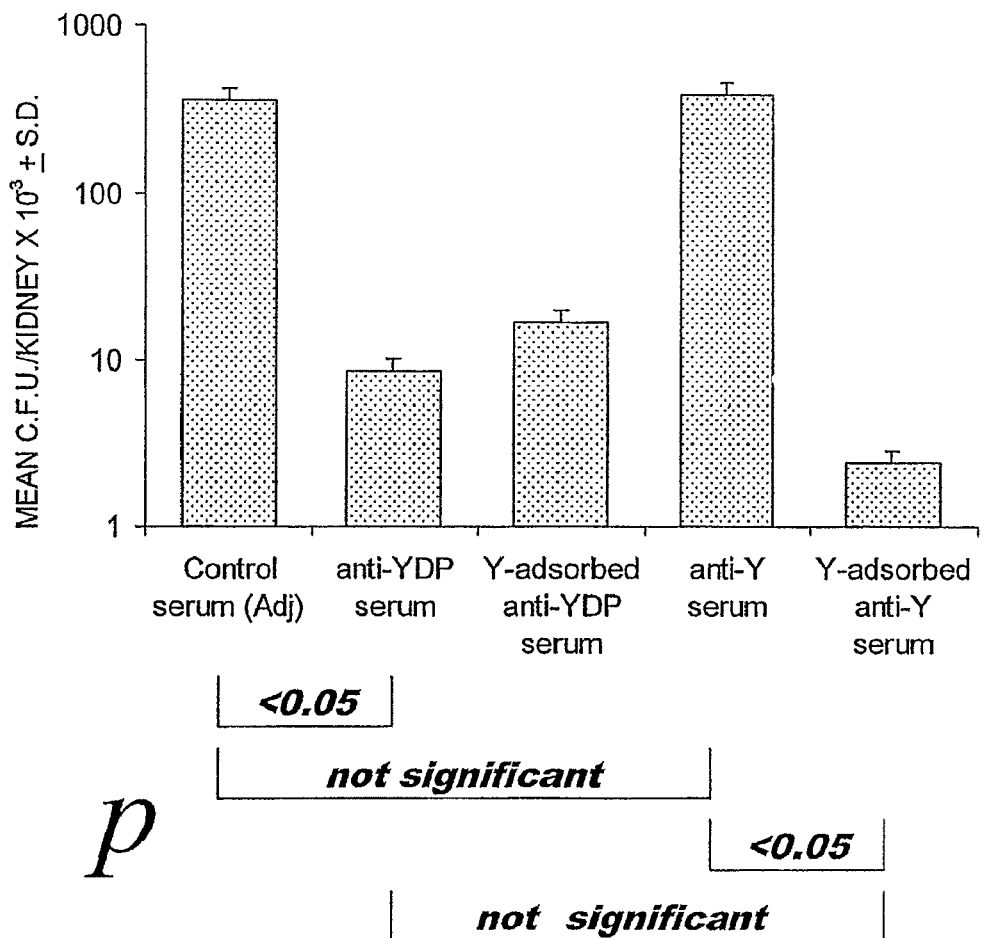
Figure 6:
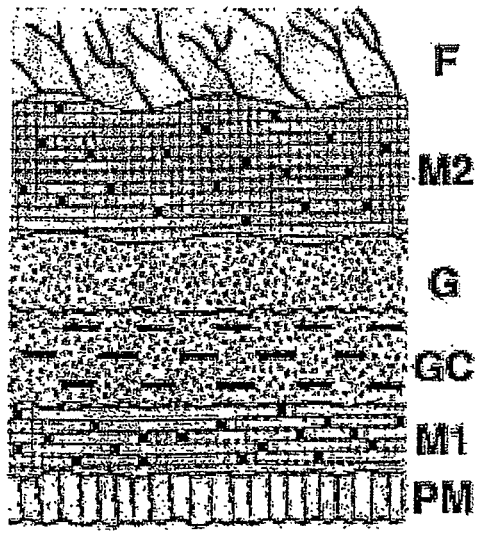
FIG. 6 is a schematic diagram of a typical *C. albicans* cell wall showing the various layers: plasma membrane (PM), zone of mannoprotein (M1), glucan-chitin (GC), glucan (G), mannoprotein (M2) and outer fibrillar layer (F).

Given the differences between Y-cells and YDP-cells, and between their sera, the substance appeared to be antibody against fungal cell surface constituents. To test this hypothesis, sera from Y-cell-immunised animals were adsorbed to Y-cells and the resulting sera were administered to SCID mice. The Y-cell-adsorbed sera had a substantial reduction of anti-MP antibodies but maintained elevated anti-β-glucan antibody levels. As shown in FIG. 5, animals receiving pre-adsorbed Y sera (column 5) had a kidney burden of about 2 logs lower than animals given non-adsorbed Y sera (column 4), and this was comparable to that of animals given the protective YDP-sera (column 2).

Thus the Y-serum contains antibodies to the yeast cell surface which are inhibitory for protection conferred by antibodies against underlying cell wall antigens (β-glucan).

These data may explain why anti-Candida sera have been found to be inconsistent in transferring protection, and why immunisation with whole inactivated cells of C. albicans has been variably protective though always stimulating an elevated DTH, cell-mediated immunity and abundant anti-Candida antibodies. The data strongly suggest that antibody-mediated protection against C. albicans not only requires the presence of the right antibody but also requires the absence of certain other antibodies.

As antibodies against abundantly-expressed cell-surface constituents are prevalent in healthy people colonized by C. albicans, the generation of antagonistic or blocking antibodies may be a mechanism by which the fungus defends itself from the eradicating capacity of other antibodies.

Antibodies to β-glucan have previously been observed in normal human sera [e.g. 174]. As they do not react with cell surface components, however, and do not obviously opsonise fungal cells, a role in the mechanism of protection had been dismissed. The anti-β-glucan IgG2 of reference 174 were specifically said to be dispensable for opsonic activity of non-encapsulated, β-glucan-exposing C. neoformans cells. The data herein invite a reconsideration of this view, as anti-β-glucan antibodies are shown to play a role in protection, at least when blocking antibodies are absent.

Even if blocking antibodies are present, the levels of anti-mannoprotein antibodies are higher than the levels of anti-glucan antibodies during natural infection and colonisation, but administering immunogenic glucans may tip the balance of inhibitory and protective antibodies in favour of protection. Furthermore, anti-C. albicans blocking antibodies may not inhibit the activity of anti-glucan antibodies against other pathogens (e.g. those whose cell walls contain glucan but not mannoprotein).

Preparation of Glucan-Carrier Conjugates

As described above, GG-zym is prepared by glucanase digestion of a glucan ghost preparation of C. albicans cells. GG-zym is pure (>99%) β-glucan. GG-zym saccharide was conjugated to CRM197 carrier protein to give 'CRM-GG'.

The conjugation process used to prepare CRM-GG starts with a reductive amination reaction by which one terminal amino group is added per chain. This amino group is subjected to reaction with di-N-hydroxysuccinimide ester of adipic acid to give an activated linker. The activated saccharides are conjugated to CRM197 protein and the conjugate intermediate is purified by ultrafiltration.

Reductive amination was performed by reacting an aqueous β-glucan saccharide solution (2 mg/ml GG-zym) with ammonium acetate (300 g/l) in the presence of sodium cyanoborohydride (28.9 g/l). The acetate and cyanoborohydride were added to the saccharide solution by funnel and the mixture was stirred until the components dissolved. pH was then adjusted to 7.2 and the mixture was transferred into a glass bottle which was sealed and incubated in a 50±1° C. water bath for 5 days. This reaction gave saccharide with a terminal amino group.

Figure 7:
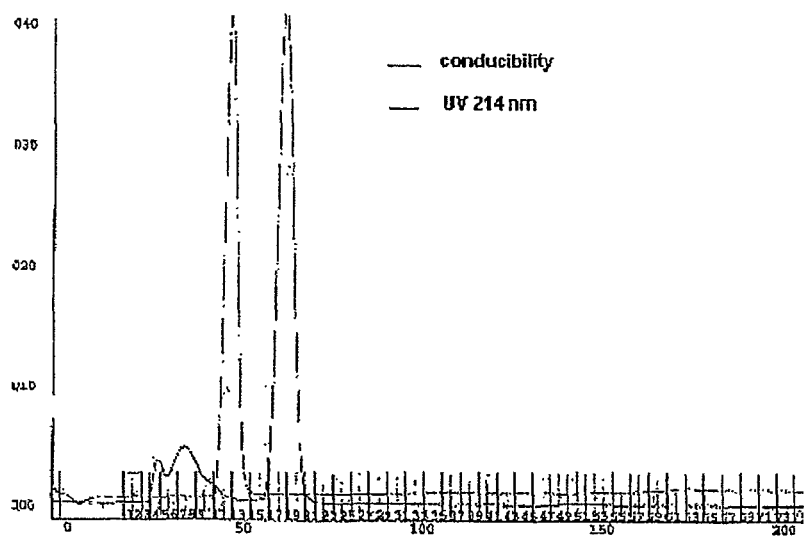
FIG. 7 shows an elution profile of a glucan-CRM197 conjugate.

The aminated saccharide was then purified by chromatography on a SEPHADEX G-10 column. All chromatography was performed at room temperature using a flow rate of 24 cm/hr, and progress was monitored by conductivity and by absorbance at 214 nm. The column was initially washed with 2 liters (5 column volumes) distilled water in order to remove the 20% ethanol storage solution. The column was then equilibrated with 2 liters of 0.2 M NaCl. Sample was loaded onto the column and fractions were collected (FIG. 7). As the saccharide has no absorbance at 214 nm, fractions were analysed by glucose analysis (phenol sulphuric method [175]) and fractions containing the saccharide were combined. The saccharide eluted from the column after 1.5 column volumes of 0.2 M NaCl.

The purified product was concentrated and purified to remove NaCl. Membranes (1K microsep, PALLFILTRON) were washed with distilled water by centrifuging at 3000 rpm for 1 hour at 4° C. on a minifuge T. Saccharide was added to the membranes and centrifuged for 3 hours at 4000 rpm to give a 0.5 ml volume. 1.5 ml distilled water was added and the mixture was centrifuged as before. This cycle was repeated until the NaCl concentration was lower than 0.02M. Samples were collated. In addition, the membranes were given a final wash with distilled water and the wash solution was added to the collated samples. The purified saccharide was analysed for glucose [175] and for amine groups [176].

The saccharide was then dried by rotary evaporation using a Buchi rotoevaporator (Model EL 131; 90 rpm) in conjunction with a KNF Neuberger Laboport vacuum pump, a Buchi 461 water bath (37° C.) and a Pharmacia Biotech multitemp III recirculating condenser chiller (4° C.). Vacuum pressure was increased slowly in order to avoid boiling. In a first phase of evaporation liquid was visible. Near the end of this phase, the majority of product appeared dry, with some bubbles within which liquid could be seen moving. The first phase ended when no obvious liquid was seen moving. The second phase of drying was an additional time under the same conditions until the material looked glassy and cracked The dried saccharide was then activated by reacting its free amino group with the di-N-hydroxysuccinimide ester (bis-NHS ester) of adipic acid. The saccharide was dissolved in DMSO to give an amine concentration of 40 mmol/L. Triethylamine (TEA) was added at a TEA:amine volume ratio of 1.113 and the mixture was stirred to homogeneity.

Succinic acid diester was dissolved in DMSO, using five times the volume of DMSO which was used to dissolve the saccharide. The amount of succinic acid diester was calculated to give a 12:1 molar ratio of succinic diester:amine groups.

With the succinic acid diester solution stirring, the saccharide mixture was slowly added and then incubated at room temperature with stirring for 1.5 to 2 hours, after which the reaction mixture was slowly added to room temparature dioxane (4 volumes in polypropylene centrifuge bottles) with stirring in order to precipitate the activated saccharide and separate it from DMSO, bis-NHS ester and TEA. After 75 minutes for precipitation, the bottles were capped and stirred for 10 minutes. The mixture was then centrifuged at 7000 g for 20 minutes at 15° C. The supernatant was decanted and the dioxane washing was repeated for a total of 5 washes. The mixture was then dried using a vacuum dryer (Lyovac GT 2). The dried saccharide was analysed for active ester [177].

Figure 8:
FIGS. 8 to 11 show analysis of the conjugate.
Figure 9:
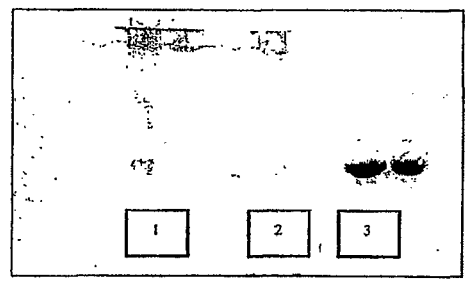

For conjugation, activated saccharide ester and CRM197 were mixed at a proportion of 20 mmol activated saccharide per mmol CRM197 in 0.01M sodium phosphate buffer, pH 7,2. The protein solution was adjusted to give a CRM197 concentration of 45 g/l and was stirred slowly in a glass bottle with a magnetic stir bar. Activated saccharide was slowly added to the bottle, which was then capped. The stirring rate was adjusted such that a small vortex formed without excess foaming. Conjugation proceeded for 14 to 22 hours. The final product was analysed by SDS-PAGE (FIG. 8; 1: MW markers; 2: CRM197; 3: conjugate; 4: supernatant conjugate) and by western blot using anti-CRM antibodies (FIG. 9; 1: supernatant conjugate; 2: conjugate; 3: CRM197).

Figure 10:
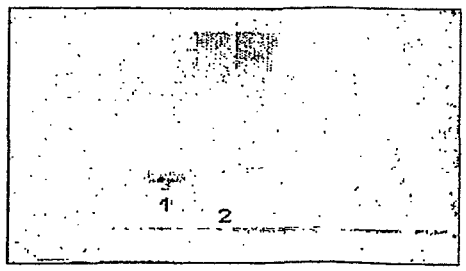
Figure 11:
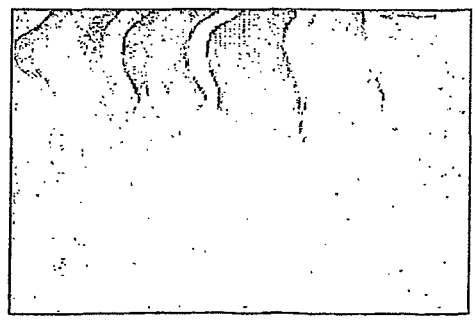

Finally, the conjugate was purified for immunogenicity studies using ultrafiltration membranes with a nominal 100 KDa cut-off (Membranes 100K Microcon SK, Amicon). Membranes were washed with 0.5 ml distilled water by centrifuging (Biofuge Picot) for 10 minutes at 2500 rpm: The conjugate was then added and centrifuged for 3 minutes at 13000 rpm. The supernatant was removed, re-added to the membrane and centrifuged for 25 minutes at 2500 rpm. 0.3 ml 0.01M sodium phosphate buffer (pH 7.2) was added and centrifuged for 25 minutes at 2500 rpm. This was repeated for a total of 7 times. The final purified product was analysed for protein [178], for glucose (high pressure anion exchange chromatography with pulsed amperometric detection), by SDS-PAGE (FIG. 10; 1: CRM197; 2: purified conjugate), and by western blot using anti-glucan antibodies (FIG. 11).

Analysis of GG-zym

The GG-zym β-glucan preparation was investigated by gel filtration chromatography and by $^1$H & $^{13}$C NMR. It was found to contain two β-glucan fractions, each representing around 50% of the GG-zym antigen weight:

Pool 1 contains basically β-1,6-glucan chains with ramifications of β-1,3-chains. The approximate degree of polymerisation (DP) of the β-1,6 chains is 36 glucose monosaccharide units, while that of the β-1,3 chains is approximately 9-10 monosaccharide units. The degree of branching (DB) is approximately 0.6.

Pool 2 contains short β-1,3-glucan chains with few β-1,6-linkages. DP is approximately 3.9 with a DB of approximately 0.03.

Immunogenicity of Conjugates

CRM-GG was tested by ELISA against immune sera from mice immunised with YDP-cells. The conjugate was highly reactive with all assayed sera, demonstrating antigenic equivalence of CRM-GG to the glucan expressed on *C. albicans* cells.

To test immunogenicity of the conjugate it was administered to CD2F1 mice according to three schedules:

Schedule A) 7 mice were each inoculated intraperitoneally with CRM-GG conjugate (20 μg protein). After 21 days, a pool of sera obtained from all immunised animals was tested by indirect ELISA. No mouse showed sign of suffering or illness during immunisation.

Schedule B) 7 mice were inoculated subcutaneously on day 0 and day 7 with CRM-GG conjugate (10 μg as protein) in incomplete Freund's adjuvant. An intraperitoneal boost was given on day 28 using 10 μg conjugate without adjuvant. Serum were pooled 7 days later and tested as for schedule A. During schedule B some animals were found suffering and one died.

Schedule C) 12 mice were inoculated subcutaneously on day 0 with CRM-GG conjugate (10 μg as protein) in complete Freund's adjuvant. Intraperitoneal boost was given on day 28 using 10 μg conjugate without adjuvant. Sera were collected 3 days later and pooled for analysis as above. No mouse showed sign of suffering or illness during immunisation.

As a negative control, un-conjugated CRM197 was administered according to Schedule B. Serum raised against unconjugated GG-zym in mouse using multiple aggressive immunisations was used as a positive control for eliciting antibody responses (2×10 μg intranasal instillation with 1 μg cholera toxin adjuvant, followed by five weekly i.p. infections of 50 μg antigen).

IgM and IgG titres of sera from immunised animals were determined by indirect ELISA using specific alkaline phosphatase-conjugated anti-mouse IgM or anti-mouse IgG secondary antibodies. Results (OD readings) for schedules A & B were as follows:

|  |  | Coating antigen | | | |
|  |  | GG-ZYM | | CRM | |
| SERUM | DILUTION | anti-IgM | anti-IgG | anti-IgM | Anti-IgG |
| anti-GG-CRM (schedule A) | 1:30 | 1.15 | — | 0.13 | 0.39 |
|  | 1:60 | 0.91 | — | 0.10 | 0.30 |
|  | 1:120 | 0.69 | — | 0.09 | 0.22 |
|  | 1:240 | 0.43 | — | — | 0.17 |
|  | 1:480 | 0.28 | — | — | 0.12 |
|  | 1:920 | 0.18 | — | — | 0.10 |
|  | 1:1920 | 0.14 | — | — | 0.10 |

-continued

| | | Coating antigen | | | |
|---|---|---|---|---|---|
| | | GG-ZYM | | CRM | |
| SERUM | DILUTION | anti-IgM | anti-IgG | anti-IgM | Anti-IgG |
| anti-GG-CRM (schedule B) | 1:30 | 1.28 | — | 0.94 | 0.84 |
| | 1:60 | 1.22 | — | 0.69 | 0.83 |
| | 1:120 | 1.18 | — | 0.47 | 0.77 |
| | 1:240 | 1.1 | — | 0.31 | 0.76 |
| | 1:480 | 0.93 | — | 0.21 | 0.73 |
| | 1:960 | 0.68 | — | 0.13 | 0.68 |
| | 1:1920 | 0.5 | — | 0.10 | 0.53 |
| anti-CRM (negative control) | 1:30 | 0.44 | 0.09 | 0.72 | 0.93 |
| | 1:60 | 0.28 | — | 0.78 | 0.8 |
| | 1:120 | 0.21 | — | 0.64 | 0.65 |
| | 1.240 | 0.16 | — | 0.50 | 0.48 |
| | 1.480 | 0.13 | — | 0.31 | 0.30 |
| | 1:960 | 0.11 | — | 0.21 | 0.20 |
| | 1:1920 | 0.1 | — | 0.20 | 0.15 |
| anti-GG-zym (positive control) | 1:30 | 0.94 | — | 0.09 | 0.09 |
| | 1:60 | 0.75 | — | " | " |
| | 1:120 | 0.54 | — | " | " |
| | 1:240 | 0.51 | — | " | " |
| | 1:480 | 0.33 | — | " | " |
| | 1:960 | 0.22 | — | " | " |
| | 1:1920 | 0.16 | — | " | " |

For schedule C, antibody ELISA titres (the highest dilution giving $OD_{405\,nm}$ value at least 2× control) and isotones were as follows:

| | Coating antigen (50 µg/ml) | | | | | | | | | |
|---|---|---|---|---|---|---|---|---|---|---|
| | GG-ZYM | | Pool 1 | | Pool 2 | | Pustulan | | Laminarin | |
| Serum | IgM | IgG | IgM | IgG | IgM | IgG | IgM | IgG | IgM | IgG |
| Anti-GG-CRM | >1920 | >1920 | >1920 | 1920 | 1920 | 480 | 480 | >>1920 | 960 | <15 |
| Anti-GG-zym | 240 | <15 | 480 | 15 | 120 | <15 | 120 | <15 | 120 | <15 |

Appreciable anti-CRM antibody titres, particularly IgG, were thus obtained following immunisation with the conjugate. More importantly, immunization also induced elevated anti-GG-zym antibody titres. Using schedules A and B, antibodies were exclusively of the IgM isotype. Using schedule C, however, animals showed consistent production of IgG antibodies against GG, in particular against the β-1-6 glucans of pool 1. Thus conjugation transformed a poor immunogen into a strong one, conferring isotype switching, and memory responses.

Analysis of Immune Responses

Sera obtained against the GG-CRM conjugate (schedule B) were tested against each pool to see if either was dominant. The same positive controls were used as before.

Indirect ELISA results were as follows, with values indicating anti-GG-CRM serum titres (IgM):

| Sera | Pool 1 | Pool 2 |
|---|---|---|
| anti-GG-CRM | >2500 | 160 |
| anti-GG-zym | 320 | 40 |

ELISA inhibition results were as follows:

| SERUM | INHIBITOR | Dose (µg/ml) | % inhibition |
|---|---|---|---|
| anti-GG-CRM (1:250 dilution) | Pool 1 | 60 | 93 |
| | | 30 | 92 |
| | | 15 | 90 |
| | | 0 | 0 |
| | Pool 2 | 60 | 62 |
| | | 30 | 53 |
| | | 15 | 30 |
| | | 0 | 0 |
| anti-GG-zym (1:80 dilution) | Pool 1 | 60 | 82 |
| | | 30 | 82 |
| | | 15 | 80 |
| | | 0 | 0 |
| | Pool 2 | 60 | 63 |
| | | 30 | 55 |
| | | 15 | 42 |
| | | 0 | 0 |

Thus the conjugate CRM-GG mainly induces antibodies against β-glucan chains present in Pool 1 i.e. higher molecular weight, primarily β-1,6-glucan.

Overall, the data obtained by mouse immunisation with the CRM-GG conjugate show that the conjugate is highly immunogenic and that the antibody response is largely superior, in terms of antibody titres, to that obtained with the GG-Zym polysaccharide alone. Importantly, antibody obtained after CRM-GG conjugate immunization has the same antigenic specificity as protective anti-β-glucan antibodies.

Cross-Reactive Immune Responses

GG-zym is derived from *C. albicans*. Mice were immunised with YDP cells of either *C. albicans* or *S. cerevisiae* using the same schedule as described above for YDP cells and the resulting sera were tested by ELISA for reactivity to GG-zym. Titres are the highest serum dilution with a reading twice that of the well without coating antigen. The secondary antibody was rabbit anti-mouse IgM.

| | Coating antigen | | |
|---|---|---|---|
| Serum | GG-Zym | Laminarin | Pustulan |
| Adjuvant only | <20 | <20 | <20 |
| YDP-*C. albicans* | >2560 | 320 | >2560 |
| YDP-*S. cerevisiae* | >2560 | >2560 | >2560 |

Antibodies raised against *S. cerevisiae* YDP cells are thus cross-reactive with *C. albicans* GG-zym antigen. The immune responses against *S. cerevisiae* and *C. albicans* are not identical, however, as anti-*C. albicans* serum is much less reactive with laminarin than the anti-*S. cerevisiae* serum.

Alternative Conjugation Process

The glucan purification and conjugation process described above was repeated with one or both of the following changes:

Rather than use 0.2 M NaCl for oligosaccharide purification after reductive amination, 20 mM NaCl was used. The alternative process involves reduced salt concentration after gel filtration and improves downstream oligosaccharide activation. The aminated saccharide elutes from the SEPHADEX G-10 column after 1.5 column volumes of 20 mM NaCl.

For conjugate purification, the first conjugate was purified (as before) by ultrafiltration using membranes with nominal 100 kDa cut-off. Other conjugates were purified by ultrafiltration using membranes with either a nominal 30 kDa or nominal 50 kDa cut-off, depending on the characteristics of the conjugates—for cross-linked high MW conjugates the 50 kDa membrane was used; for conjugates without cross-linking the 30 kDa membrane was used. The 30 kDa & 50 kDa membranes were used with either a Centricon™ (centrifugal filter unit) technique or a tangential flow technique.

For the Centricon™ technique, 30 kDa or 50 kDa membranes were obtained from Millipore™ for use with MINIFUGE T (Heraeus Sepatech). The device was washed by centrifuging 3 ml distilled water for 10 minutes at 3500 rpm. The conjugate was then centrifuged at 3500 rpm for 3 minutes. The supernatant was removed and added to the device followed by 25 minutes of centrifugation at 3500 rpm. 1.5 ml 0.01M sodium phosphate buffer (pH 7.2) was then added, and centrifuged for 25 minutes at 3500 rpm. This procedure was performed 8 times in total.

For tangential flow ultrafiltration, a Holder Labscale (Millipore) apparatus was used with 505U Pumps (W. Marlow) and PLCIC-C 30 kDa cut-off 50 cm$^2$ membranes (Millipore). The system was washed with distilled water until the pH of the permeate was <7.00. The system was then equilibrated with 100 ml of 0.01M sodium phosphate buffer (pH 7.2). The sample was then loaded into the holder and the following ultrafiltration conditions were applied: pressure in 25.7 psi {1 psi=6894.757 Pa}; pressure out 18.4 psi {1 psi=6894.757 Pa}; flow rate 7.6 ml/min. Forty diafiltration volumes of 0.01M sodium phosphate buffer (pH 7.2) were used. Finally, the sample was placed in another vessel and the system was washed, first with 0.1 M NaOH, then with water and finally with 0.05M NaOH.

Separation of Pools 1 & 2

As mentioned above, the GG-zym β-glucan preparation contains two main fractions—pools 1 & 2. These two pools can be separated by gel filtration.

Figure 12:
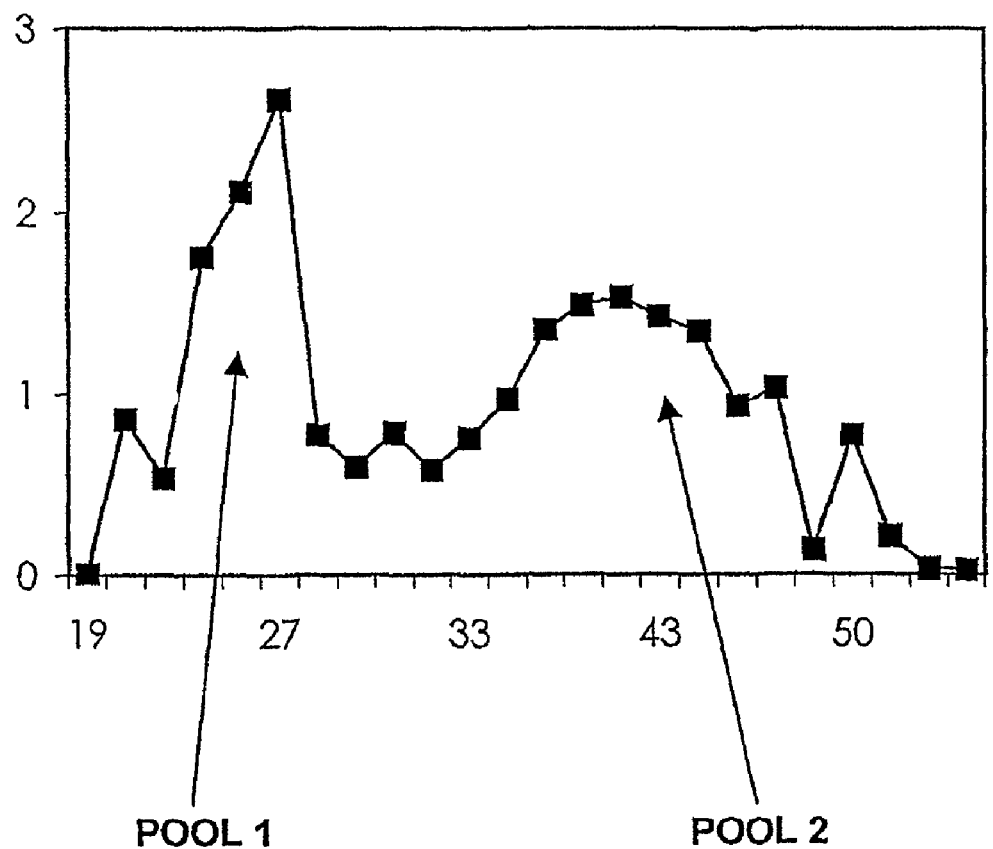
FIG. 12 shows the elution profile of a Bio-Gel P-2 column. Fraction numbers are shown on the X-axis, with $OD_{214nm}$ being on the Y-axis.

Using a Pharmacia™ FPLC system operating at room temperature and a flow rate of 0.37 cm/hr, a Bio-Gel P-2 Fine column (Bio Rad) was equilibrated with 450 ml of 0.02M PBS (pH 7.4). The mixed GG-zym sample was loaded onto the column and eluted with 1.0 column volume of 0.02M PBS (pH 7.4). After collecting fractions, the column was stripped with the same buffer for 1.5 column volumes, then washed with 3 column volumes of distilled water and with 3 column volumes of 20% ethanol as storage solution. The output from the column was monitored by conductivity and by absorbance at 214 nm, as described above. As shown in FIG. 12, pools 1 and 2 elute separately.

The two different glucan populations can be used separately to make conjugates using the procedure described above.

Laminarin Conjugate

For comparative purposes, a further conjugate was made using CRM197 carrier and laminarin. Laminarin has a similar glucan structure to pool 2 of GG-zym (i.e. 1,3-β-glucans), but it has a higher average degree of polymerisation of about 30.

The process for making the laminarin conjugate is the same as used for the GG-Zym, except for oligosaccharide purification after reductive amination. For laminarin, the process used a Holder Labscale apparatus (Millipore) using 505U Pumps (W. Marlow) and a PLCBC-C 3KD cut-off 50$^2$ membrane (Millipore). The apparatus was washed with distilled water until the pH of the permeate is <7.00. The apparatus was then equilibrated with 100 ml of 0.5M NaCl, and the sample was then loaded into the holder and the following ultrafiltration conditions were applied: pressure in 19 psi {1 psi=6894.757 Pa}; pressure out 13 psi {1 psi=6894.757 Pa}; flow rate 0.6 ml/min. Thirteen diafiltration volumes of 0.5M NaCl were used, followed by six diafiltration volumes of H$_2$O. Finally, the sample was placed in another vessel and the system was washed, first with 0.1M NaOH, then with water and finally with 0.05M NaOH.

Figure 13:
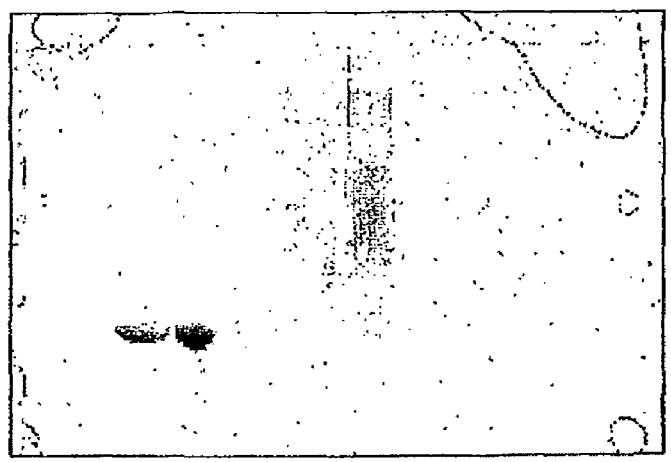
FIG. 13 shows SDS-PAGE analysis of a laminarin-$CRM_{197}$ conjugate.

FIG. 13 shows SDS-PAGE of the laminarin conjugate. The two spots at the left show unconjugated CRM$^{197}$ carrier, and the two spots at the right show the conjugate.

Summary

Whole intact *C. albicans* yeast cells do not confer protective immunity against *C. albicans*, whereas protease-treated cells can confer protective immunity.

Anti-*Candida* protection induced by protease-treated cells is in part mediated by antibodies, with anti-β-glucan antibodies playing an important role.

Protective, serum-transferable, antibody-mediated protection against *C. albicans* can be negated by immune responses to cell-surface located, immunodominant fungal antigens. Thus immunisation with whole intact cells elicits cell-surface reactive, antagonistic or blocking antibodies.

Protein-glucan conjugates are effective immunogens.

Anti-glucan antibodies raised against one organism can cross-react with glucans from another organism.

It will be understood that the invention has been described by way of example only and modifications may be made whilst remaining within the scope and spirit of the invention.

REFERENCES (The Contents of which are Hereby Incorporated by Reference)

[1] Deepe (1997) *Clin. Microbiol. Rev.* 10:585-596.
[2] Polonelli et al. (2000) *Med Mycol* 38 Suppl 1:281-292.
[3] Casadevall (1995) *Infect. Immun.* 63:4211-4218.
[4] Cassone (2000) *Nippon Ishinkin Gakkai Zasshi* 41(4):219.
[5] U.S. Pat. No. 5,578,309 (see also WO95/31998).
[6] U.S. Pat. No. 6,309,642 (see also WO98/23287).
[7] WO01/51517
[8] Pitson et al. (1996) *Biochem. J.* 316:81-845.
[9] Tokunaka et al. (1999) *Carbohydr Res* 316:161-172.
[10] Ley (2001) *Discover the Beta Glucan Secret* . . . . ISBN 1890766186.
[11] Lindberg (1999) *Vaccine* 17 Suppl 2:S28-36
[12] Buttery & Moxon (2000) *J R Coll Physicians Lond* 34:163-8
[13] Ahmad & Chapnick (1999) *Infect Dis Clin North Am* 13:113-33, vii
[14] Goldblatt (1998) *J. Med. Microbiol.* 47:563-567
[15] EP-B-0 477 508
[16] U.S. Pat. No. 5,306,492

[17] WO98/42721
[18] Dick et al. in *Conjugate Vaccines* (eds. Cruse et al.) Karger, Basel, 1989, Vol. 10, 48-114
[19] Hermanson *Bioconjugate Techniques*, Academic Press, San Diego Calif. (1996)
[20] Ramsay et al. (2001) *Lancet* 357(9251):195-6
[21] U.S. Pat. No. 4,761,283
[22] U.S. Pat. No. 4,356,170
[23] U.S. Pat. No. 4,882,317
[24] U.S. Pat. No. 4,695,624
[25] *Mol. Immunol.*, 1985, 22, 907-919
[26] EP-A-0208375
[27] Bethell G. S. et al., *J. Biol. Chem.*, 1979, 254, 2572-4
[28] Hearn M. T. W., *J. Chromatogr.*, 1981, 218, 509-18
[29] WO00/10599
[30] Geyer et al., Med. Microbiol. Immunol, 165: 171-288 (1979).
[31] U.S. Pat. No. 4,057,685.
[32] U.S. Pat. Nos. 4,673,574; 4,761,283; 4,808,700.
[33] U.S. Pat. No. 4,459,286.
[34] U.S. Pat. No. 4,965,338
[35] U.S. Pat. No. 4,663,160.
[36] *Research Disclosure*, 453077 (January 2002)
[37] EP-A-0372501
[38] EP-A-0378881
[39] EP-A-0427347
[40] WO93/17712
[41] WO94/03208
[42] WO98/58668
[43] EP-A-0471177
[44] WO00/56360
[45] WO91/01146
[46] WO00/61761
[47] WO01/72337
[48] WO99/42130
[49] WO96/40242
[50] Lei et al. (2000) *Dev Biol (Basel)* 103:259-264
[51] WO00/38711
[52] Breedveld (2000) *Lancet* 355(9205):735-740.
[53] Gorman & Clark (1990) *Semin. Immunol.* 2:457-466
[54] Jones et al., *Nature* 321:522-525 (1986)
[55] Morrison et al., *Proc. Natl. Acad. Sci, U.S.A.*, 81:6851-6855 (1984)
[56] Morrison and Oi, *Adv. Immunol.*, 44:65-92 (1988)
[57] Verhoeyer et al., *Science* 239:1534-1536 (1988)
[58] Padlan, *Molec. Immun.* 28:489-498 (1991)
[59] Padlan, *Molec. Immunol.* 31(3):169-217 (1994).
[60] Kettleborough, C. A. et al., *Protein Eng.* 4(7):773-83 (1991).
[61] WO 98/24893
[62] WO 91/10741
[63] WO 96/30498
[64] WO 94/02602
[65] U.S. Pat. No. 5,939,598.
[66] Kieber-Emmons (1998) *Immunol Res* 17:95-108
[67] Fleuridor et al. J Immunol 2001 Jan. 15; 166(2):1087-96
[68] Valadon et al. J Immunol 1998 Aug. 15; 161(4):1829-36
[69] Bodanszky (1993) *Principles of Peptide Synthesis* (ISBN: 0387564314).
[70] Fields et al. (eds.) (1997) *Methods in Enzymology, Volume 289: Solid-Phase Peptide Synthesis*. ISBN: 0121821900.
[71] Chan & White (2000) *Fmoc Solid Phase Peptide Synthesis: A Practical Approach*. ISBN: 0199637245.
[72] Kullmann (1987) *Enzymatic Peptide Synthesis*. ISBN: 0849368413.
[73] Ibba (1996) *Biotechnol Genet Eng Rev* 13:197-216.
[74] Robinson & Torres (1997) *Seminars in Immunology* 9:271-283.
[75] Donnelly et al. (1997) *Annu Rev Immunol* 15:617-648.
[76] Scott-Taylor & Dalgleish (2000) *Expert Opin Investig Drugs* 9:471-480.
[77] Apostolopoulos & Plebanski (2000) *Curr Opin Mol Ther* 2:441-447.
[78] Ilan (1999) *Curr Opin Mol Ther* 1:116-120.
[79] Dubensky et al. (2000) *Mol Med* 6:723-732.
[80] Robinson & Pertmer (2000) *Adv Virus Res* 55:1-74.
[81] Donnelly et al. (2000) *Am J Respir Crit. Care Med* 162(4 Pt 2):S190-193.
[82] Davis (1999) *Mt. Sinai J. Med.* 66:84-90.
[83] Strugnell et al. (1997) *Immunol Cell Biol* 75(4):364-369.
[84] Brunham et al. (2000) *J Infect Dis* 181 Suppl 3:S538-43.
[85] Svanholm et al. (2000) *Scand J Immunol* 51(4):345-53.
[86] Kieber-Emmons et al. J Immunol 2000 Jul. 15; 165(2): 623-627
[87] Beninati et al. (2000) *Nature Biotechnology* 18:1060-1064.
[88] Kazmierski (1999) *Peptidomimetics Protocols*. ISBN: 0896035174.
[89] Abell (1999) *Advances in Amino Acid Mimetics and Peptidomimetics*. ISBN: 0762306149.
[90] U.S. Pat. No. 5,331,573 (Balaji).
[91] Goodman et al. (2001) Biopolymers 60:229-245.
[92] Hruby & Balse (2000) *Curr Med Chem* 7:945-970.
[93] Ribka & Rich (1998) *Curr Opin Chem Biol* 2:441-452.
[94] Gennaro (2000) *Remington: The Science and Practice of Pharmacy*. 20th edition, ISBN: 0683306472.
[95] Almeida & Alpar (1996) *J. Drug Targeting* 3:455-467.
[96] *Vaccine design: the subunit and adjuvant approach*, eds. Powell & Newman, Plenum Press 1995 (ISBN 0-306-44867-X).
[97] WO90/14837.
[98] WO00/07621.
[99] WO99/27960.
[100] European patent applications 0835318, 0735898 and 0761231.
[101] Krieg (2000) *Vaccine* 19:618-622; Krieg (2001) *Curr opin Mol Ther* 2001 3:15-24; WO96/02555, WO98/16247, WO98/18810, WO98/40100, WO98/55495, WO98/37919 and WO98/52581 etc.
[102] WO99/52549.
[103] WO01/21207.
[104] WO01/21152.
[105] WO00/62800.
[106] WO00/23105.
[107] WO99/11241.
[108] WO98/57659.
[109] Del Giudice et al. (1998) *Molecular Aspects of Medicine*, vol. 19, number 1.
[110] Johnson et al. (1999) *Bioorg Med Chem Lett* 9:2273-2278.
[111] International patent application WO00/50078.
[112] Singh et al. (2001) *J. Cont. Rele.* 70:267-276.
[113] Covacci & Rappuoli (2000) *J. Exp. Med.* 19:587-592.
[114] WO93/18150.
[115] Covacci et al. (1993) *Proc. Natl. Acad. Sci. USA* 90: 5791-5795.
[116] Tummuru et al. (1994) *Infect. Immun.* 61:1799-1809.
[117] Marchetti et al. (1998) *Vaccine* 16:33-37.
[118] Telford et al. (1994) *J. Exp. Med.* 179:1653-1658.
[119] Evans et al. (1995) *Gene* 153:123-127.
[120] WO96/01272 & WO96/01273, especially SEQ ID NO:6.
[121] WO97/25429.

[122] WO98/04702.
[123] WO99/24578.
[124] WO99/36544.
[125] WO99/57280.
[126] WO00/22430.
[127] Tettelin et al. (2000) *Science* 287:1809-1815.
[128] WO96/29412.
[129] Pizza et al. (2000) *Science* 287:1816-1820.
[130] WO01/52885.
[131] Bjune et al. (1991) *Lancet* 338(8775):1093-1096.
[132] Fukasawa et al. (1999) *Vaccine* 17:2951-2958.
[133] Rosenqvist et al. (1998) *Dev. Biol. Stand.* 92:323-333.
[134] Costantino et al. (1992) *Vaccine* 10:691-698.
[135] Costantino et al. (1999) *Vaccine* 17:1251-1263.
[136] Watson (2000) *Pediatr Infect Dis J* 19:331-332.
[137] Rubin (2000) *Pediatr Clin North Am* 47:269-285, v.
[138] Jedrzejas (2001) *Microbiol Mol Biol Rev* 65:187-207.
[139] Bell (2000) *Pediatr Infect Dis J*19:1187-1188.
[140] Iwarson (1995) *APMIS* 103:321-326.
[141] Gerlich et al. (1990) *Vaccine* 8 Suppl:S63-68 & 79-80.
[142] Hsu et al. (1999) *Clin Liver Dis* 3:901-915.
[143] Gustafsson et al. (1996) *N Engl. J. Med.* 334:349-355.
[144] Rappuoli et al. (1991) *TIBTECH* 9:232-238.
[145] *Vaccines* (1988) eds. Plotkin & Mortimer. ISBN 0-7216-1946-0.
[146] Del Guidice et al. (1998) *Molecular Aspects of Medicine* 19:1-70.
[147] WO02/02606.
[148] Kalman et al. (1999) *Nature Genetics* 21:385-389.
[149] Read et al. (2000) *Nucleic Acids Res* 28:1397-406.
[150] Shirai et al. (2000) *J. Infect. Dis.* 181(Suppl 3):S524-S527.
[151] WO99/27105.
[152] WO00/27994.
[153] WO00/37494.
[154] WO99/28475.
[155] Ross et al. (2001) *Vaccine* 19:4135-4142.
[156] Sutter et al. (2000) *Pediatr Clin North Am* 47:287-308.
[157] Zimmerman & Spann (1999) *Am Fam Physician* 59:113-118, 125-126.
[158] Dreesen (1997) *Vaccine* 15 Suppl:S2-6.
[159] *MMWR Morb Mortal Wkly Rep* 1998 Jan. 16; 47(1):12, 19.
[160] Anderson (2000) *Vaccine* 19 Suppl 1:S59-65.
[161] Kahn (2000) *Curr Opin Pediatr* 12:257-262.
[162] Crowe (1995) *Vaccine* 13:415-421.
[163] McMichael (2000) *Vaccine* 19 Suppl 1:S101-107.
[164] Schuchat (1999) *Lancet* 353(9146):51-6.
[165] WO02/34771.
[166] Dale (1999) *Infect Dis Clin North Am* 13:227-43, viii.
[167] Ferretti et al. (2001) *PNAS USA* 98: 4658-4663.
[168] Kuroda et al. (2001) *Lancet* 357(9264):1225-1240; see also pages 1218-1219.
[169] *J. Toxicol Clin Toxicol* (2001) 39:85-100.
[170] Demicheli et al. (1998) *Vaccine* 16:880-884.
[171] Stepanov et al. (1996) *J Biotechnol* 44:155-160.
[172] Wills et al. (2000) *Emerging Therapeutic Targets* 4:1-32.
[173] Yuan et al. (1997) *PNAS USA* 94:2483-2488.
[174] Keller et al. (1994) *Infect Immun* 62:215-220.
[175] Dubois et al. (1956) *Anal. Chem.* 28:350-356.
[176] Habeeb (1966) *Analytical Biochemistry* 14:328-336.
[177] Miran et al. (1982) *Analytical Biochemistry* 126:433-435.
[178] Smith et al. (1985) *Analytical Biochemistry* 150:76-85.

The invention claimed is:

1. An immunogenic composition comprising an immunogenic component conjugated to a bacterial toxin or toxoid, wherein
    (a) the immunogenic component is a glucan polymer that has a molecular weight of less than 100 kDa, wherein said glucan is
        i) a glucan from a protease-treated fungal cell,
        ii) a glucan from a mannoprotein depleted fungal cell, or
        iii) a pure glucan; and
    (b) when the composition is administered to a mammal, it elicits protective anti-glucan antibodies but does not elicit antibodies which inhibit the protective efficacy of the anti-glucan antibodies.

2. The composition of claim 1, wherein the glucan is β-glucan.

3. The composition of claim 2, wherein the glucan contains one or more (β-1,6-linkages.

4. The composition of claim 1, wherein the glucan is a fungal glucan.

5. The composition of claim 2, wherein the glucan is a β-glucan derived from the cell wall of a *Candida*.

6. The composition of 5, wherein the glucan is a β-glucan derived from the cell wall of *C. albicans*.

7. The immunogenic composition of claim 6, further comprising a *C. albicans* secreted aspartyl proteinase (SAP2).

8. The composition of claim 1, wherein the composition is substantially free of mannoprotein.

9. The composition of claim 1, further comprising an adjuvant.

10. The composition of claim 1, wherein the composition is depleted of mannoprotein.

11. The composition of claim 10, wherein the composition is depleted of mannoprotein by treatment of a fungal cell wall with a protease.

12. An immunogenic composition comprising a β-glucan from the cell wall of *C. albicans* that has been treated with glucanase, conjugated to $CRM_{197}$, wherein when the composition is administered to a mammal, it elicits protective anti-glucan antibodies but does not elicit antibodies which inhibit the protective efficacy of the anti-glucan antibodies.

13. The immunogenic composition of claim 12, further comprising a *C. albicans* secreted aspartyl proteinase (SAP2).

14. An immunogenic composition comprising a conjugate that comprises a β-glucan conjugated to $CRM_{197}$, wherein the conjugate is prepared by a method comprising:
    (a) obtaining a preparation of *C. albicans* cells;
    (b) treating said preparation with glucanase;
    (c) conjugating said glucanase-treated preparation with $CRM_{197}$ to produce a β-glucan-$CRM_{197}$ conjugate; and
    (d) purifying said conjugate.

15. The immunogenic composition of claim 14, further comprising a *C. albicans* secreted aspartyl proteinase (SAP2).

16. A method for raising an antibody response in a mammal, comprising administering a composition according to claim 1 to the mammal.

17. A method for treating or preventing a microbial infection in a mammal, comprising administering to the mammal a composition according to claim 1.

18. The method claim 16, wherein the mammal is a human.

19. The method of claim 17, wherein the mammal is a human.

20. The method of claim 17, wherein the microbial infection is caused by *Candida*.

21. The method of claim 20, wherein the microbial infection is candidosis.

* * * * *